US006469076B1

(12) United States Patent
Momoda et al.

(10) Patent No.: US 6,469,076 B1
(45) Date of Patent: Oct. 22, 2002

(54) CHROMENE COMPOUNDS

(75) Inventors: Junji Momoda; Yasuko Komuro, both of Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 09/744,305

(22) PCT Filed: May 18, 2000

(86) PCT No.: PCT/JP00/03200

§ 371 (c)(1), (2), (4) Date: Apr. 30, 2001

(87) PCT Pub. No.: WO00/71544

PCT Pub. Date: Nov. 30, 2000

(30) Foreign Application Priority Data

May 24, 1999 (JP) ............................................ 11-144072

(51) Int. Cl.[7] ..................... C07D 311/96; C07D 413/14; C08F 2/44

(52) U.S. Cl. ............................. 524/86; 524/87; 524/89; 524/107; 525/185; 525/186; 525/330.3; 525/330.5; 526/328; 544/70; 549/60; 549/331

(58) Field of Search ............................... 544/70; 549/60, 549/331; 525/185; 524/86

(56) References Cited

FOREIGN PATENT DOCUMENTS

DE          19902771     * 12/1999

* cited by examiner

*Primary Examiner*—Robert W. Ramsuer
(74) *Attorney, Agent, or Firm*—Sherman & Shalloway

(57) ABSTRACT

A photochromic compound which by itself develops a color tone of a neutral tint, exhibits a large fading rate and offers a good photochromic light resistance. A novel chromene compound has a basic structure as shown below in which a condensed ring formed by a particular divalent group bonded to carbon atoms at the fifth and sixth positions of a pyran ring, is spiro-bonded to the first position of an indene ring, a particular divalent group is bonded to carbon atoms at the fifth and sixth positions of a chromene ring to form a condensed ring, and a particular substituent is bonded to a carbon atom at the second position of the chromene ring,

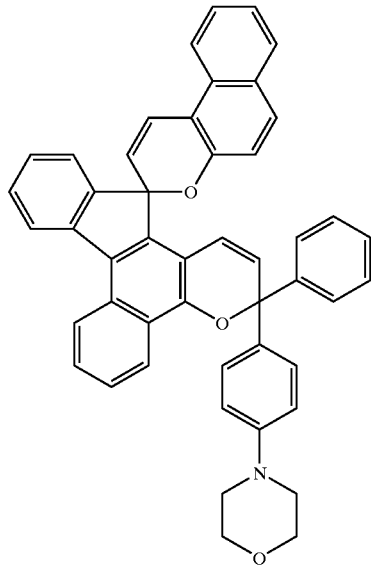

14 Claims, No Drawings

CHROMENE COMPOUNDS

TECHNICAL FIELD

The present invention relates to a novel chromene compound and to a photochromic polymerizable composition containing the chromene compound.

The invention further relates to a photochromic material containing the chromene compound and, particularly, to a photochromic optical material.

BACKGROUND ART

Photochromism is a phenomenon that is drawing attention in these several years, and is a reversible action of a compound which quickly changes its color when it is irradiated with light containing ultraviolet rays such as sunlight or light of a fluorescent lamp and resumes its initial color when it is no longer irradiated with light but is placed in a dark place. The compound having this property is called photochromic compound. Various compounds have so far been synthesized without, however, any particular common nature in their structures.

The specification of PCT Patent Application Laid-Open Specification WO 96/14596 discloses a chromene compound represented by the following formula (A),

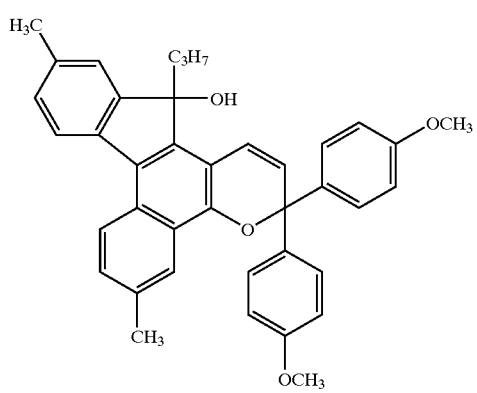

(A)

This chromene compound, however, has a small color fading rate, is colored to a considerable degree (also called coloring after aged) in a state of not being irradiated with light after it is used as a photochromic material for extended periods of time, and loses color density when it is irradiated with light.

Further, the specification of PCT Patent Application Laid-Open Specification WO 97/48762 discloses a chromene compound represented by the following formula (B),

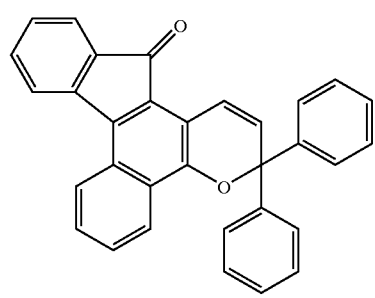

(B)

This chromene compound, however, has a problem of a low fading rate.

Further, Examples 4, 7 and 5 of German Patent Application Laid-Open DE 19902771 A1 disclose chromene compounds represented by the following formulas (C), (D) and (E).

However, these chromene compounds have low color-developing sensitivities, and their fading rates are not of satisfactory levels, either.

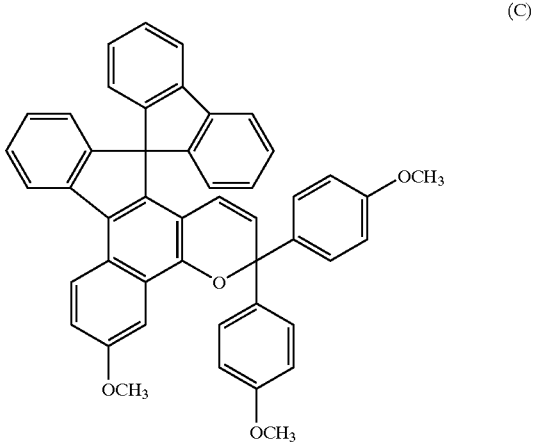

(C)

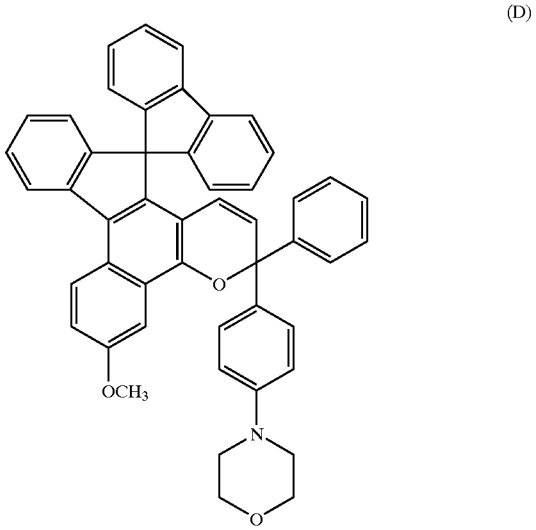

(D)

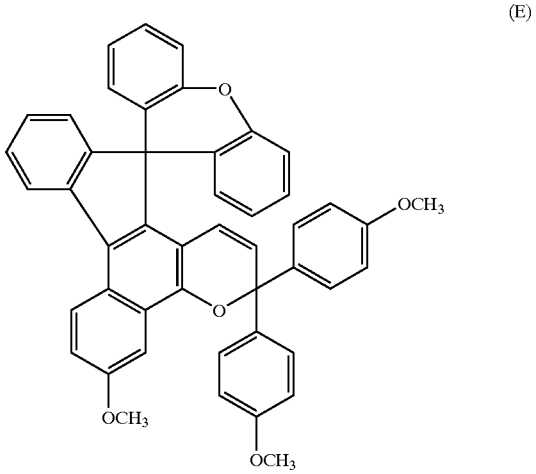

(E)

The compounds disclosed in the above-mentioned publications exhibit bluish color tones by themselves. When it is desired to obtain neutral tints such as grey and brown that are preferred in, for example, the photochromic lenses, it is necessary to use in combination other photochromic compounds that exhibit yellow or red color tones.

DISCLOSURE OF THE INVENTION

It is therefore an object of the present invention to provide a chromene compound which by itself develops a color tone of a neutral tint, exhibits further improved photochromic properties compared with the above-mentioned compounds, exhibits a fast fading rate, shows less color after aged, permits a small decrease in the photochromic properties as represented by a decrease in the color density, i.e., exhibits excellent photochromic fatigue resistance.

The present invention was proposed to accomplish the above object, and a novel chromene compound was completed by the present inventors based on a knowledge that it exhibits a color tone of a neutral tint by itself, exhibits a fast fading rate, is colored little after aged, and exhibits excellent photochromic fatigue resistance.

That is, the present invention is concerned with a chromene compound represented by the following general formula (1),

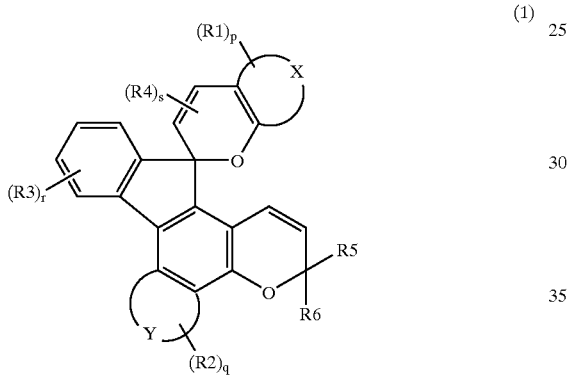

(1)

wherein a divalent group represented by the following formula (2),

(2)

and a divalent group represented by the following formula (3),

(3)

are aromatic hydrocarbon groups or unsaturated heterocyclic groups independently from each other;

a substituent R1 of the group represented by the above formula (2) is an alkyl group, a hydroxyl group, an alkoxyl group, an aralkoxyl group, an amino group, a substituted amino group, a cyano group, a nitro group, substituted or unsubstituted aryl group, a halogen atom, a trifluoromethyl group, an aralkyl group, a monovalent heterocyclic group bonded to the ring of the group represented by the above formula (2) through the carbon atom, a monovalent substituted or unsubstituted heterocyclic group having a nitrogen atom as a hetero atom and bonded to the ring of the group represented by the above formula (2) through said nitrogen atom, or a monovalent condensed heterocyclic group in which said heterocyclic group is condensed with an aromatic hydrocarbon ring or an aromatic heterocyclic ring, and p is an integer of 0 to 3;

a substituent R2 of the group represented by the above formula (3) is an alkyl group, a hydroxyl group, an alkoxyl group, an aralkoxyl group, an amino group, a substituted amino group, a cyano group, a nitro group, substituted or unsubstituted aryl group, a halogen atom, a trifluoromethyl group, an aralkyl group, a monovalent heterocyclic group bonded to an indene ring through the carbon atom, a monovalent substituted or unsubstituted heterocyclic group having a nitrogen atom as a hetero atom and bonded to the ring of the group represented by the above formula (3)through said nitrogen atom, or a monovalent condensed heterocyclic group in which said heterocyclic group is condensed with an aromatic hydrocarbon ring or an aromatic heterocyclic ring, and q is an integer of 0 to 3;

a substituent R3 of the indene ring is an alkyl group, a hydroxyl group, an alkoxyl group, an aralkoxyl group, an amino group, a substituted amino group, a cyano group, a nitro group, substituted or unsubstituted aryl group, a halogen atom, a trifluoromethyl group, an aralkyl group, a monovalent heterocyclic group bonded to the indene ring through the carbon atom, a monovalent substituted or unsubstituted heterocyclic group having a nitrogen atom as a hetero atom and bonded to the indene ring through said nitrogen atom, or a monovalent condensed heterocyclic group in which said heterocyclic group is condensed with an aromatic hydrocarbon ring or an aromatic heterocyclic ring, and r is an integer of 0 to 3;

a substituent R4 of the pyran ring is an alkyl group, a hydroxyl group, an alkoxyl group, an aralkoxyl group, an amino group, a substituted amino group, a cyano group, a nitro group, a substituted or unsubstituted aryl group, a halogen atom, a trifluoromethyl group, an aralkyl group a monovalent heterocyclic group bonded to the pyran ring through the carbon atom, is a monovalent substituted or unsubstituted heterocyclic group having a nitrogen atom as a hetero atom and bonded to the pyran ring through said nitrogen atom, or a monovalent condensed heterocyclic group in which said heterocyclic group is condensed with an aromatic hydrocarbon ring or an aromatic heterocyclic ring, and s is an integer of 0 to 3;

each of R5 and R6 is, independently from each other, groups represented by the following formula (4),

(4)

wherein R7 is a substituted or unsubstituted aryl group or a substituted or unsubstituted heteroaryl group, R8 is a hydrogen atom, an alkyl group or a halogen atom, and n is an integer of 1 to 3;

a group represented by the following formula (5),

wherein R9 is a substituted or unsubstituted aryl group or a substituted or unsubstituted heteroaryl group, and m is an integer of 1 to 3;

a substituted or unsubstituted aryl group, substituted or unsubstituted heteroaryl group, or an alkyl group, wherein R5 and R6 together may constitute an aliphatic hydrocarbon ring or an aromatic hydrocarbon ring.

As represented by the above general formula (1), the chromene compound of the present invention has a basic structure in which:

① a condensed ring which is formed by bonding a divalent group represented by the above general formula (2) to the pyran ring at it's fifth and sixth position is spiro-bonded to the indene ring at it's first position;

② a divalent group represented by the above formula (3) is bonded to carbon atoms at the fifth and sixth positions of the chromene ring to form a condensed ring; and ③ particular substituents represented by R5 and R6 are bonded to a carbon atom at the second position of the chromene compound.

The above-mentioned excellent effects are obtained by the combination of the above three features.

In particular, the chromene compound of the present invention is preferably the one represented by the following general formula (6),

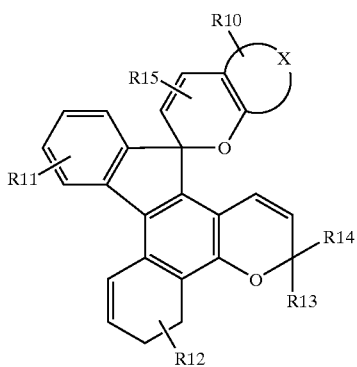

wherein a divalent group represented by the following formula (2),

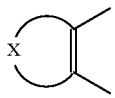

is an aromatic hydrocarbon group or an unsaturated heterocyclic group;

each of R10, R11, R12 and R15 is, independently from each other, a hydrogen atom; an alkyl group having 1 to 4 carbon atoms; an alkoxyl group having 1 to 5 carbon atoms; an aralkoxyl group having 6 to 10 carbon atoms; a mono-substituted or di-substituted amino group having, as a substituent, an alkyl group with 1 to 4 carbon atoms or an aryl group with 6 to 10 carbon atoms; a cyano group; an aryl group having 6 to 10 carbon atoms; a substituted aryl group having 6 to 10 carbon atoms (without including carbon atoms of the substituent) and having, as a substituent, an alkyl group having 1 to 4 carbon atoms or an alkoxy group having 1 to 5 carbon atoms; a halogen atom; a substituted or unsubstituted heterocyclic group having a nitrogen atom as a hetero atom and bonded to a ring of the group represented by the above formula (2) or to the indene ring, pyran ring or naphthalene ring through the nitrogen atom; or a condensed heterocyclic group in which said heterocyclic group is condensed with an aromatic hydrocarbon ring or an aromatic heterocyclic ring; and each of R13 and R14 is, independently from each other, an aryl groups having 6 to 10 carbon atoms; or a substituted aryl group having, as a substituent, (i) an alkyl group with 1 to 4 carbon atoms (ii) an alkoxy group with 1 to 5 carbon atoms, (iii) a substituted or unsubstituted heterocyclic group which has a nitrogen atom as a hetero atom and is bonded to the aryl group through the nitrogen atom, or (iv) a condensed hetrocyclic group in which said heterocyclic group is condensed with an aromatic hydrocarbon ring or an aromatic heterocyclic ring; said substituted aryl group having 6 to 10 carbon atoms (without including the carbon atoms of the substituent).

Among the chromene compounds represented by the above general formula (6), it is desired that:

the chromene compound is the one of which the group represented by the above formula (2) is an aromatic hydrocarboxyl group having 6 to 18 carbon atoms;

one of R13 and R14 is a substituted aryl group having at least one substituent selected from the group consisting of (a) a mono-substituted or di-substituted amino group which has, as a substituent, an alkyl group with 1 to 4 carbon atoms or an aryl group with 6 to 10 carbon atoms, (b) a morpholino group, (c) a piperidino group, (d) a pyrrolidinyl group, (e) a piperadino group, (f) an N-methylpiperadino group and (g) an indolinyl group, said substituted aryl group having 6 to 10 carbon atoms (without including carbon atoms of the substituent), and the other one is an aryl group with 6 to 10 carbon atoms.

Another invention is concerned with a photochromic material containing the chromene compound represented by the above general formula (1) and, particularly, a photochromic optical material containing the above chromene compound.

According to the present invention, further, there is provided a photochromic polymerizable composition containing the above-mentioned chromene compound, a polymerizable monomer (particularly, a (meth)acrylic acid ester compound) and, as required, a polymerization initiator.

BEST MODE FOR CARRYING OUT THE INVENTION

Chromene Compound

In the above general formula (1), a group represented by the following formula (2),

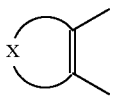

(2)

and a group represented by the following formula (3),

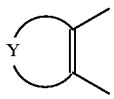

(3)

are aromatic hydrocarbon groups or unsaturated heterocyclic groups independently from each other.

Though there is no particular limitation, it is desired that the aromatic hydrocarbon group has 6 to 18 carbon atoms. Preferred examples of the aromatic hydrocarbon group are substituted aromatic hydrocarbon groups comprising condensed rings of one or two to four benzene rings, such as phenylene group, naphthylene group, phenanthrylene group, tolylene group and xylene group.

Though there is no particular limitation, the unsaturated heterocyclic group is a heterocyclic group of which the ring is condensed with a 5-membered ring or a 6-membered ring containing oxygen atom, sulfur atom or nitrogen atom, or is further condensed with a benzene ring. Preferred examples of the unsubstituted unsaturated heterocyclic group include nitrogen-containing heterocyclic groups such as pyridylene group, quinolylene group, pyrolylene group and indolylene group; oxygen-containing heterocyclic groups such as furylene group and benzofurylene group; and sulfur-containing heterocyclic groups such as thienylene group and benzothienylene group.

The aromatic hydrocarbon group or the unsaturated heterocyclic group represented by the above formulas (2) and (3) may have a substituent R1 and a substituent R2, respectively.

Here, R1 is an alkyl group, a hydroxyl group, an alkoxyl group, an aralkoxyl group, an amino group, a substituted amino group, a cyano group, a nitro group, a substituted or unsubstituted aryl group, a halogen atom, a trifluoromethyl group, an aralkyl group, a monovalent heterocyclic group bonded to the ring of the group represented by the above formula (2) through a carbon atom, a monovalent substituted or unsubstituted heterocyclic group having a nitrogen atom as a hetero atom and is bonded to the ring of the group represented by the above formula (2) through the nitrogen atom, or a monovalent condensed heterocyclic group in which the heterocyclic group is condensed with an aromatic hydrocarbon ring or an aromatic heterocyclic ring. Described below are the substituents R1 of which the structures have been known, but excluding the hydroxyl group, amino group, cyano group, nitro group and trifluoromethyl group.

(a) Though there is no particular limitation, the alkyl group usually has 1 to 4 carbon atoms. Preferred examples of the alkyl group include methyl group, ethyl group, n-propyl group, isopropyl group, n-butyl group, sec-butyl group and t-butyl group.

(b) Though there is no particular limitation, the alkoxyl group generally has 1 to 5 carbon atoms. Preferred examples of the alkoxyl group include methoxy group, ethoxy group, n-propoxy group, isopropoxy group, n-butoxy group, sec-butoxy group and t-butoxy group.

(c) Though there is no particular limitation, the aralkoxyl group preferably has 6 to 10 carbon atoms. Preferred examples of the aralkoxyl group include phenoxy group and naphthoxy group.

(d) Though there is no particular limitation, the substituted amino group is preferably an alkylamino group substituted with an alkyl group or an aryl group, a dialkylamino group, an arylamino group or a diarylamino group. Preferred examples of the substituted amino group include methylamino group, ethylamino group, phenylamino group, dimethylamino group, diethylamino group and diphenylamino group.

(e) Though there is no particular limitation, the substituted or unsubstituted aryl group is preferably a substituted aryl group having 6 to 10 carbon atoms. Preferred examples of the unsubstituted aryl group include phenyl group and naphthyl group.

As the substituted aryl group, there can be exemplified the one in which one or two or more hydrogen atoms of the unsubstituted aryl group are substituted with substituents. As the substituent, there can be exemplified alkyl group, alkoxyl group, substituted amino group, aryl group, substituted or unsubstituted heterocyclic group having a nitrogen atom as a hetero atom and is bonded to the aryl group through the nitrogen atom, and a condensed heterocyclic group in which the heterocyclic group is condensed with an aromatic hydrocarbon ring or an aromatic heterocyclic ring. As the alkyl group, alkoxyl group and substituted amino group, there can be exemplified those represented by R1 above. The substituted or unsubstituted heterocyclic group and condensed heterocyclic group are the same as the "substituted or unsubstituted heterocyclic group having a nitrogen atom as a hetero atom and is bonded to the ring of the group represented by the above formula (2) through the nitrogen atom, and the condensed heterocyclic group in which the heterocyclic group is condensed with an aromatic hydrocarbon ring or an aromatic heterocyclic ring" represented by R1, except that the ring bonded through the nitrogen atom is changed from the indene ring into an aromatic ring of the aryl group. Details will be described later.

(f) As the halogen atom, there can be exemplified fluorine atom, chlorine atom, bromine atom or iodine atom.

(g) Though there is no particular limitation, it is desired that the aralkyl group has 7 to 11 carbon atoms. Preferred examples of the aralkyl group include benzyl group, phenylethyl group, phenylpropyl group and phenylbutyl group.

(h) Though there is no particular limitation, the monovalent heterocyclic group bonded to the ring of the group represented by the above formula (2) through a carbon atom is, preferably, thienyl group, furyl group or pyrolyl group.

(i) There is no particular limitation on the substituted or unsubstituted heterocyclic group having a nitrogen atom as a hetero atom and is bonded to the ring of the group represented by the above formula (2) through the nitrogen atom or on the condensed heterocyclic group in which the heterocyclic group is condensed with an aromatic hydrocarbon ring or an aromatic heterocyclic ring. Here, however, it is desired that the number of carbon atoms constituting the heterocyclic group is from 2 to 10 and, particularly, from 2 to 6. The heterocyclic ring may further contain a hetero atom in addition to the nitrogen atom bonded to the ring of the group represented by the above formula (2). Though there is no particular limitation, the hetero atom is an oxygen atom, a sulfur atom or a nitrogen atom. As the substituent for these groups, further, there can be exemplified the same substitutes as those for the substituted aryl group described in (e) above. Preferred examples of the substituted or unsubstituted heterocyclic group having a nitrogen atom as a hetero atom which is bonded to the ring of the group represented by the above formula (2) or of the condensed heterocyclic group in which the heterocyclic group is condensed with an aromatic hydrocarbon ring or an aromatic heterocyclic ring, include morpholino group, piperidino group, pyrolydinyl group, piperadino group, N-methylpiperadino group and indolinyl group.

p which represents the number of substituents R1 is an integer of from 0 to 3. There is no particular limitation on the position where R1 is bonded and there is no particular limitation on the total number thereof, either. It is, however, desired that the number of R1 is not larger than 2. When p is 2 or 3, R1 may be different from each other.

Like those of R1, further, the substituent R2 for the group represented by the above formula (3) may be alkyl group, hydroxyl group, alkoxyl group, aralkoxyl group, amino group, substituted amino group, cyano group, nitro group, substituted or unsubstituted aryl group, halogen atom, trifluoromethyl group, aralkyl group, monovalent heterocyclic group bonded to the ring of the group represented by the formula (3) through a carbon atom, monovalent substituted or unsubstituted heterocyclic group having a nitrogen atom as a hetero atom and is bonded to the ring of the group represented by the above formula (3) through the nitrogen atom, or monovalent condensed heterocyclic group in which the heterocyclic group is condensed with an aromatic hydrocarbon ring or an aromatic heterocyclic ring.

The above "substituted or unsubstituted heterocyclic group having a nitrogen atom as a hetero atom and is bonded to the ring of the group represented by the above formula (3) through the nitrogen atom, or the condensed heterocyclic group in which the heterocyclic group is condensed with an aromatic hydrocarbon ring or an aromatic heterocyclic ring" and "the monovalent heterocyclic group bonded to the ring of the group represented by the above formula (3) through a carbon atom", are the same as the "substituted or unsubstituted heterocyclic group having a nitrogen atom as a hetero atom and is bonded to the ring of the group represented by the above formula (2) through the nitrogen atom, or the condensed heterocyclic group in which the heterocyclic group is condensed with an aromatic hydrocarbon ring or an aromatic heterocyclic ring" and the "monovalent heterocyclic group bonded to the ring of the group represented by the above formula (2) through the carbon atom" represented by R1, with only a difference in the rings to which the nitrogen atoms and carbon atoms are bonded.

q which represents the number of substituents R2 is an integer of from 0 to 3. There is no particular limitation on the position where R2 is bonded and there is no particular limitation on the total number thereof, either. It is, however, desired that the number of R2 is not larger than 2. When q is 2 or 3, R2 may be different from each other.

Further, the substituents represented by R3 and R4 may also be bonded to the indene ring and pyran ring in the above general formula (1).

Here, R3 and R4 are, independently from each other, monovalent heterocyclic groups bonded to the indene ring or the pyran ring through alkyl group, hydroxyl group, alkoxyl group, aralkoxyl group, amino group, substituted amino group, cyano group, nitro group, substituted or unsubstituted aryl group, halogen atom, trifluoromethyl group, aralkyl group or carbon atom, are monovalent substituted or unsubstituted heterocyclic groups having a nitrogen atom as a hetero atom and are bonded to the indene ring or the pyran ring, or are monovalent condensed heterocyclic groups in which the heterocyclic groups are condensed with an aromatic hydrocarbon ring or an aromatic heterocyclic ring.

Here, the "monovalent heterocyclic group bonded to the indene ring or the pyran ring through the carbon atom" and the "substituted or unsubstituted heterocyclic group having a nitrogen atom as a hetero atom and is bonded to the indene ring or the pyran ring through the nitrogen atom, or the condensed heterocyclic group in which the heterocyclic group is condensed with an aromatic hydrocarbon ring or an aromatic heterocyclic ring" are the same as the "monovalent heterocyclic group bonded to the ring of the group represented by the above formula (2) through a carbon atom" and the "substituted or unsubstituted heterocyclic group having a nitrogen atom as a hetero atom and is bonded to the ring of the group represented by the above formula (2) through the nitrogen atom, or the condensed heterocyclic group in which the heterocyclic group is condensed with an aromatic hydrocarbon ring or an aromatic heterocyclic ring" represented by R1, with only a difference in the rings to which the nitrogen atoms and carbon atoms are bonded.

r and s which represent the numbers of substituents R3 and R4 are integers of from 0 to 3. There is no particular limitation on the positions where R3 and R4 are bonded and there is no particular limitation on the total numbers thereof, either. It is, however, desired that the numbers of R3 and R4 are not larger than 2, respectively. When r and s are each 2 or 3, each of R3 and R4 may be different from each other.

In the above general formula (1), R5 and R6 are, independently from each other, groups represented by the following formula (4),

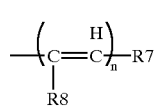
(4)

wherein R7 is a substituted or unsubstituted aryl group, or a substituted or unsubstituted heteroaryl group, R8 is a hydrogen atom, an alkyl group or a halogen atom, and n is an integer of 1 to 3, groups represented by the following formula (5),

(5)

wherein R9 is a substituted or unsubstituted aryl group, or a substituted or unsubstituted heteroaryl group, and m is an integer of 1 to 3, or substituted or unsubstituted aryl groups, substituted or unsubstituted heteroaryl groups, or alkyl groups. Here, further, R5 and R6 are not limited to these groups only but may be combined together to form an aliphatic hydrocarbon ring or an aromatic hydrocarbon ring.

In the above formula (4), R7 is a substituted or unsubstituted aryl group, or a substituted or unsubstituted heteroaryl group. As the substituted or unsubstituted aryl group, there can be exemplified the same substituted or unsubstituted aryl groups represented by R1 above.

In the substituted aryl group, there is no particular limitation on the position on where the substituent is bonded and there is no particular limitation on the total number thereof, either. When the aryl group is a phenyl group, however, a third position or a fourth position is preferred. When the aryl group is a naphthyl group, a fourth position or a sixth position is preferred.

Though there is no particular limitation on the above unsubstituted heteroaryl group, a heteroaryl group having 4 to 12 carbon atoms is preferred. Concrete examples include thienyl group, furyl group, pyrolinyl group, pyridyl group, benzothienyl group, benzofuranyl group and benzopyrolinyl group. As the substituted heteroaryl group, there can be exemplified the unsubstituted heteroaryl group of which one or two or more hydrogen atoms are substituted by the same substituents as those of the substituted aryl group represented by R1 above. There is no particular limitation on the positions on where the substituents are bonded and there is no particular limitation on the total numbers thereof, either.

In the above formula (4), R8 is a hydrogen atom, an alkyl group or a halogen atom. Preferred examples of the alkyl group include methyl group, ethyl group and propyl group. Concrete examples of the halogen atom include fluorine atom, chlorine atom, bromine atom and iodine atom.

In the above formula (4), n is an integer of 1 to 3. From the standpoint of availability of the starting material, however, it is desired that n is 1.

Preferred examples of the group represented by the above formula (4) include phenyl-ethylene group, (4-(N,N-dimethylamino)phenyl)-ethenyl group, (4-(N,N-diethylamino)phenyl)-ethenyl group, (4-morpholinophenyl)-ethenyl group, (4-piperidinophenyl)-ethenyl group, (4-eurolidinophenyl)-ethenyl group, (4-methoxyphenyl)-ethenyl group, (4-methylphenyl)-ethenyl group, (2-(N,N-dimethylamino)phenyl)-ethenyl group, (2-methoxyphenyl)-ethenyl group, phenyl-1-methylethenyl group, (4-(N,N-dimethylamino)phenyl)-1-methylethenyl group, (4-methoxyphenyl)-1-methylethenyl group, phenyl-1-fluoroethenyl group, (4-(N,N-dimethylamino)phenyl)-1-fluoroethenyl group, 2-thienyl-ethenyl group, 2-furyl-ethenyl group, 2-(N-methyl)pyrolinyl-ethenyl group, 2-benzothienyl-ethenyl group, 2-benzofuranyl-ethenyl group and 2-(N-methyl) indolyl-ethenyl group.

In the above formula (5), further, R9 is a substituted or unsubstituted aryl group or a substituted or unsubstituted heteroaryl group. These groups are the same as those represented by R7 above.

There is no particular limitation on m in the above formula (5) provided it is an integer of 1 to 3. From the standpoint of easy availability of the starting material, however it is desired that m is 1.

Preferred examples of the group represented by the above formula (5) include phenyl-ethlenyl group, (4-(N,N-dimethylamino)phenyl)-ethenyl group, (4-(N,N-diethylamino)phenyl)-ethenyl group, (4-morpholinophenyl)-ethenyl group, (4-piperidinophenyl)-ethenyl group, (4-eurolidinophenyl)-ethenyl group, (4-methoxyphenyl)-ethenyl group, (4-methylphenyl)-ethenyl group, (2-(N,N-dimethylamino)phenyl)-ethenyl group, (2-methoxyphenyl)-ethenyl group, 2-thienyl-ethenyl group, 2-furyl-ethenyl group, 2-(N-methyl)pyrolinyl-ethenyl group, 2-benzothienyl-ethenyl group, 2-benzofuranyl-ethenyl group and 2-(N-methyl)indolyl-ethenyl group.

The substituted or unsubstituted aryl groups or the substituted or unsubstituted heteroaryl groups represented by R5 and R6 are the same as those represented by R7 above.

The alkyl groups represented by R5 and R6 are the same as those represented by R1 above.

There is no particular limitation on the aliphatic hydrocarbon ring formed by R5 and R6 in combination. However, preferred examples of the ring include adamantilidene ring, bicyclononylidene ring and norbornylidene ring.

There is no particular limitation on the aromatic hydrocarbon ring formed by R5 and R6 in combination. However, preferred examples of the ring include fluorene ring and the like ring.

Here, it is desired that at least one of R5 and R6 is a substituted or unsubstituted aryl group or a substituted or unsubstituted heteroaryl group, or a group thereof having another group.

It is particularly desired that at least one of R5 and R6 is any one of the following groups (i) to (ix):

(i) a substituted aryl group or a substituted heteroaryl group having a substituted amino group as a substituent;

(ii) a substituted aryl group or a substituted heteroaryl group having, as a substituent, a substituted or unsubstituted heterocyclic group having nitrogen atom as a hetero atom and is bonded to the aryl group or the heteroaryl group through the nitrogen atom;

(iii) a substituted aryl group or a substituted heteroaryl group having, as a substituent, a condensed heterocyclic group of which the aromatic hydrocarbon ring or the aromatic heterocyclic ring is condensed with the substituted or unsubstituted heterocyclic ring of (ii) above;

(iv) a group represented by the above formula (4) in which R7 is a substituted aryl group or a substituted heteroaryl group having a substituted amino group as a substituent;

(v) a group represented by the above formula (4) in which R7 is a substituted aryl group or a substituted heteroaryl group having a nitrogen atom as a hetero atom and having, as a substituent, a substituted or unsubstituted heterocyclic group of which the aryl group or the heteroaryl group is bonded to the nitrogen atom;

(vi) a group represented by the above formula (4) in which R7 is a substituted aryl group or a substituted heteroaryl group having, as a substituent, a condensed heterocyclic group in which an aromatic hydrocarbon ring or an aromatic heterocyclic ring is condensed with the substituted or unsubstituted heterocyclic group of (v) above;

(vii) a group represented by the above formula (5) in which R9 is a substituted aryl group or a substituted heteroaryl group having a substituted amino group as a substituent;

(viii) a group represented by the above formula (5) in which R9 is a substituted aryl group or a substituted heteroaryl group having a nitrogen atom as a hetero atom and having, as a substituent, a substituted or unsubstituted heterocyclic group of which the aryl group or the heteroaryl group is bonded to the nitrogen atom; or (ix) a group represented by the above formula (5) in which R9 is a substituted aryl group or a substituted heteroaryl group having, as a substituent, a condensed heterocyclic group of which the aromatic hydrocarbon ring or the aromatic heterocyclic ring is condensed with the substituted or unsubstituted heterocyclic group of (viii) above.

In the substituted aryl groups in (i) to (iii) above, there is no particular limitation on the position where a substituent is substituted and there is no particular limitation on the total number thereof, either. When the aryl group that is the substituent is a phenyl group, however, it is desired that the substitution takes place at the third or the fourth position, and the number thereof is 1. Preferred examples of the aryl group include 4-(N,N-dimethylamino)phenyl group, 4-(N,N-diethylamino)phenyl group, 4-(N,N-diphenylamino)phenyl group, 4-morpholinophenyl group, 4-piperidinophenyl group and 3-(N,N-dimethylamino)phenyl group.

In the substituted heteroaryl groups in (i) to (iii) above, further, there is no particular limitation on the position where a substituent is substituted and there is no particular limitation on the total number thereof, either. It is, however, desired that the number thereof is 1. Preferred examples of the heteroaryl group include 4-(N,N-dimethylamino)thienyl group, 4-(N,N-diethylamino)furyl group, 4-(N,N-diphenylamino)thienyl group, 4-morpholinopyrolinyl group, 6-piperidinobenzothienyl group and 6-(N,N-dimethylamino)benzofuranyl group.

In the groups represented by the formula (4) in (iv) to (vi) above, R7 represents the same substituted aryl groups or the substituted heteroaryl groups as those of (i) to (iii) above. Preferred examples of the group represented by the formula (4) include (4-(N,N-dimethylamino)phenyl)-ethenyl group, (4-(N,N-diethylamino)phenyl)-ethenyl group, (4-morpholinophenyl)-ethenyl group, (4-piperidinophenyl)-ethenyl group, (4-eurolidinophenyl)-ethenyl group, (2-(N,N-dimethylamino)phenyl)-ethenyl group, (4-(N,N-dimethylamino)phenyl)-1-methylethenyl group, and (4-(N,N-dimethylamino)phenyl)-1-fluoroethenyl group.

In the groups represented by the formula (5) in (vii) to (ix) above, R9 represents the same substituted aryl groups or the substituted heteroaryl groups as those of (i) to (iii) above. Preferred examples of the group represented by the formula (5) include (4-(N,N-dimethylamino)phenyl)-ethenyl group, (4-(N,N-diethylamino)phenyl)-ethenyl group, (4-morpholinophenyl)-ethenyl group, (4-piperidinophenyl)-ethenyl group, (4-eurolidinophenyl)-ethenyl group, (2-(N,N-dimethylamino)phenyl)-ethenyl group, 2-(N-methyl) indolyl-ethenyl group, and (4-(N-methylpiperadino) phenyl)-ethenyl group.

From the standpoint of effect according to the present invention, it is desired that the chromene compound is the one represented by the following general formula (6),

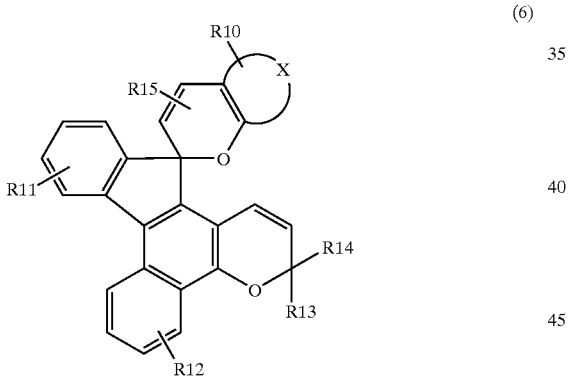

(6)

wherein a group represented by the following formula (2)

(2)

is as defined in the above general formula (1); R10, R11, R12 and R15 are, independently from each other, hydrogen atoms; alkyl groups having 1 to 4 carbon atoms; alkoxyl groups having 1 to 5 carbon atoms; aralkoxyl groups having 6 to 10 carbon atoms; mono-substituted or di-substituted amino groups having, as a substituent, an alkyl group with 1 to 4 carbon atoms or aryl group with 6 to 10 carbon atoms; cyano groups; aryl groups having 6 to 10 carbon atoms; substituted aryl groups having 6 to 10 carbon atoms (without including carbon atoms of the substituent) substituted with an alkyl group having 1 to 4 carbon atoms or with an alkoxyl group having 1 to 5 carbon atoms as a substituent; halogen atoms; substituted or unsubstituted heterocyclic groups having a nitrogen atom as a hetero atom and bonded to a ring of the group represented by the above formula (2) or to the indene ring, pyran ring or naphthalene ring through the nitrogen atom, or condensed heterocyclic groups in which the heterocyclic group is condensed with an aromatic hydrocarbon ring or an aromatic heterocyclic ring; and each of R13 and R14 is, independently from each other, an aryl groups having 6 to 10 carbon atoms; or a substituted aryl group having, as a substituent, (i) an alkyl group with 1 to 4 carbon atoms (ii) an alkoxy group with 1 to 5 carbon atoms, (iii) a substituted or unsubstituted heterocyclic group which has a nitrogen atom as a hetero atom and is bonded to the aryl group through the nitrogen atom, or (iv) a condensed hetrocyclic group in which said heterocyclic group is condensed with an aromatic hydrocarbon ring or an aromatic heterocyclic ring; said substituted aryl group having 6 to 10 carbon atoms (without including the carbon atoms of the substituent).

In the above general formula (6), further, it is most desired from the standpoint of fading rate that the group represented by the above formula (2) is an aromatic hydrocarbon group having 6 to 18 carbon atoms; and one of R13 and R14 is a substituted aryl group having at least one substituent selected from the group consisting of (a) a mono-substituted or di-substituted amino group which has, as a substituent, an alkyl group with 1 to 4 carbon atoms or an aryl group with 6 to 10 carbon atoms, (b) a morpholino group, (c) a piperidino group, (d) a pyrrolidinyl group, (e) a piperadino group, (f) an N-methylpiperadino group and (g) an indolinyl group, said substituted aryl group having 6 to 10 carbon atoms (without including carbon atoms of the substituent), and the other one is an aryl group with 6 to 10 carbon atoms.

The following compounds are the most preferred examples of the chromene compound of the present invention.

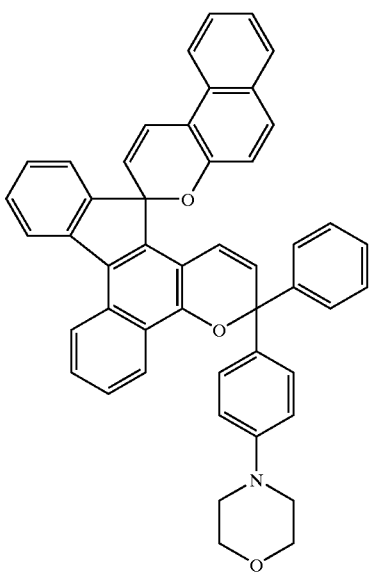

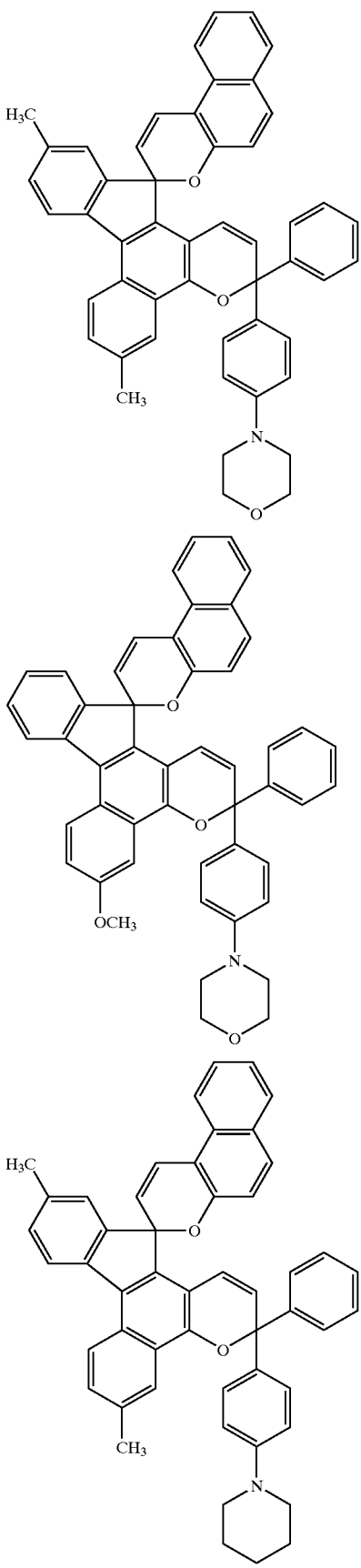

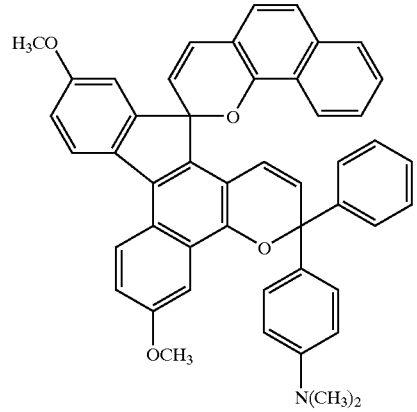

The compound represented by the above general formula (1) of the present invention usually exists as a colorless or pale yellowish solid or viscous liquid at normal temperature and under normal pressure, and can be confirmed by the following means (a) to (c).

(a) Measurement of a proton nuclear magnetic resonance spectrum ($^1$H-NMR) indicates peaks based on an aromatic proton and an alkene proton. near δ5.0 to 9.0 ppm and peaks based on protons of an alkyl group and an alkylene group near δ1.0 to 4.0 ppm. Upon relatively comparing the spectrum intensities, further, the numbers of protons in the bonding groups can be known.

(b) The compositions of the corresponding products can be determined by the elemental analysis.

(c) Measurement of a $^{13}$C-nuclear magnetic resonance spectrum ($^{13}$C-NMR) indicates a peak based on a carbon atom of an aromatic hydrocarbon group near δ110 to 160 ppm, peaks based on carbon atoms of an alkene and an alkine near δ80 to 140 ppm, and peaks based on carbon atoms of an alkyl group and an alkylene group near δ20 to 80 ppm. [Preparation of Chromene Compound]

There is no particular limitation on the method of preparing a chromene compound represented by the general formula (1) of the present invention, and any synthesizing method may be employed. Described below is a representative method that is generally preferably employed.

According to this method, a chromene compound represented by the above general formula (1) is obtained by reacting a propargyl alcohol-chromene derivative (hereinafter abbreviated as precursor chromene compound) represented by the following general formula (7),

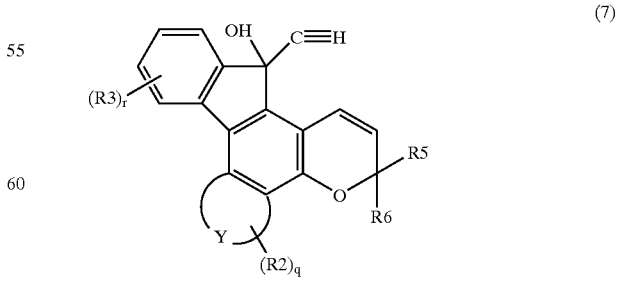

(7)

wherein R2, R3, R5, R6, q, r and the divalent group represented by the following formula (3),

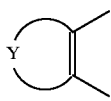

(3)

are as defined in the above general formula (1), with a hydroxyl derivative represented by the following general formula (8),

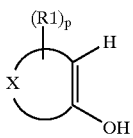

(8)

wherein R1, p and the divalent group represented by the following formula (2),

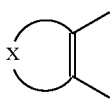

(2)

are as defined in the above general formula (1), in the presence of an acid catalyst.

There is no particular limitation on the method of synthesizing the compound (precursor chromene compound) represented by the above general formula (7) which can be preferably produced by, for example, the following method.

That is, a hydroxy-fluorenone derivative represented by the general formula (9),

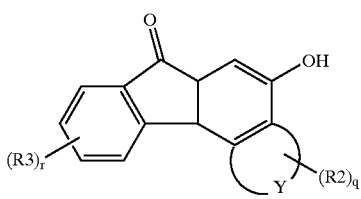

(9)

wherein R2, R3, q, r and the group of the following formula (3),

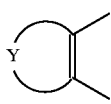

(3)

are as defined in the above general formula (1), and a propargyl alcohol derivative represented by the general formula (10),

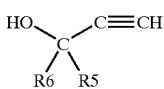

(10)

wherein R5 and R6 are as defined in the general formula (1),
are reacted together under an acidic condition to obtain a fluorenone-chromene derivative represented by the general formula (11),

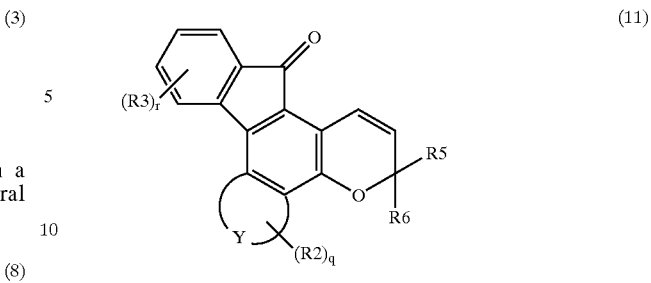

(11)

wherein R2, R3, R5, R6, q, r and the group of the following formula (3),

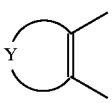

(3)

are as defined in the general formula (1), and, then, the compound represented by the general formula (11) is reacted with a metal acetylene compound such as lithium acetylide to thereby preferably synthesize the precursor chromene compound. Here, when a hydroxy-fluorene derivative having a substituent on a Y-ring of the hydroxy-fluorenone derivative is used, there can be synthesized a precursor chromene compound having substituents on the respective Y-rings.

The compound (precursor chromene compound) represented by the above general formula (7) is reacted with the hydroxy derivative represented by the general formula (8) in the presence of an acid catalyst under, for example, the following conditions. That is, the reaction ratio of these two kinds of compounds can be selected over a wide range. Generally, however, the reaction ratio is selected over a range of from 1:10 to 10:1 (molar ratio). As the acid catalyst, there can be used sulfuric acid, benzenesulfonic acid, p-toluenesulfonic acid or acidic alumina in an amount over a range of from 0.1 to 10 parts by weight per 100 parts by weight of the total of the reaction substrates represented by the above general formulas (7) and (8). The reaction temperature is preferably from 0 to 200° C., and the solvent is a nonprotonic organic solvent, such as N-methylpyrrolidone, dimethylformamide, tetrahydrofuran, benzene or toluene.

There is no particular limitation on the method of refining the product. For example, the product is refined by silica gel column and, then, by recrystallization.

When there is used the precursor chromene compound of the formula (7) or a compound obtained by substituting a hydrogen atom of the ethenyl group of the propargyl alcohol derivative of the formula (10) with a group R4 (as defined in the formula (1)), a chromene compound substituted by the group R4 can be easily produced among the chromene compounds of the present invention.

Photochromic Material

The chromene compound represented by the above general formula (1) of the present invention dissolves well in a general organic solvent such as toluene, chloroform or tetrahydrofuran. When the chromene compound represented by the general formula (1) is dissolved in the above solvent, the solution is usually nearly colorless and transparent, quickly develops a color when it is irradiated with sunlight or ultraviolet rays, and reversibly returns to the initial colorless state when it is no longer irradiated with light, thus exhibiting a good photochromic action.

The photochromic action of the compound of the general formula (1) exhibits similar properties even in a high molecular solid matrix. Such a high molecular solid matrix may be any one provided the chromene compound represented by the general formula (1) of the invention homogeneously disperses therein. Optically preferred examples are thermoplastic resins such as methyl polyacrylate, ethyl polyacrylate, methylpolymethacrylate, ethyl polymethacrylate, polystyrene, polyacrylonitrile, polyvinyl alcohol, polyacrylamide, poly(2-hydroxyethylmethacrylate), polydimethylsiloxane and polycarbonate.

There can be further exemplified (meth)acrylic acid ester compounds having plural (meth)acryloyloxy groups, such as ethylene glycol diacrylate, diethylene glycol dimethacrylate, triethylene glycol dimethacrylate, tetraethylene glycol dimethacrylate, nonaethylene glycol dimethacrylate, tetradecaethylene glycol dimethacrylate, ethylene glycol bisglicidylmethacrylate, bisphenol A dimethacrylate, 2,2-bis(4-methacryloyloxyethoxyphenyl)propane, and 2,2-bis(3,5-dibromo-4-methacryloyloxyethoxyphenyl)propane; multi-valent allyl compounds such as diallyl phthalate, diallyl terephthalate, diallyl isophthalate, diallyl tartarate, diallyl epoxysuccinate, diallyl fumarate, diallyl chloroendoate, diallyl hexaphthalate, diallyl carbonate, diallyl diglycol carbonate, and trimethylolpropanetriallyl carbonate; multi-valent thioacrylic acid and multi-valent thiomethacrylic acid ester compounds such as 1,2-bis(methacryloylthio)ethane, bis(2-acryloylthioethyl)ether, and 1,4-bis(methacryloylthiomethyl)benzene; (meth)acrylic acid ester compounds having one or more functional groups other than the (meth)acryloyloxy group, such as glycidyl acrylate, glycidyl methacrylate, β-methylglicidyl methacrylate, bisphenol A-monoglycidylether methacrylate, 4-glycidyloxy methacrylate, 3-(glicidyl-2-oxyethoxy)-2-hydroxypropyl methacrylate, 3-(glycidyloxy-1-isopropyloxy)-2-hydroxypropyl acrylate, and 3-glycidyloxy-2-hydroxypropyloxy)-2-hydroxypropyl acrylate; and thermosetting resins obtained by polymerizing radically polymerizable polyfunctional monomers such as divinyl benzene and the like.

There can be further exemplified copolymers of these monomers with unsaturated carboxylic acids such as acrylic acid, methacrylic acid and maleic anhydride; acrylic acid and methacrylic acid ester compounds such as methyl acrylate, methyl methacrylate, benzyl methacrylate, phenyl methacrylate, and 2-hydroxyethyl methacrylate; fumaric acid ester compounds such as diethyl fumarate and diphenyl fumarate; thioacrylic acid and thiomethacrylic acid ester compounds such as methylthio acrylate, benzylthio acrylate and benzylthio methacrylate; or radically polymerizable monofunctional monomers such as vinyl compounds like styrene, chlorostyrene, methyl styrene vinyl naphthalene, α-methylstyrene dimer, and bromostyrene.

There is no particular limitation on the method of dispersing the chromene compound represented by the general formula (1) of the invention in the high molecular solid matrix, and any generally employed method can be used. For example, the above thermoplastic resin and the chromene compound are kneaded together in a molten state and are dispersed in a resin. Or, the chromene compound is dissolved in the polymerizable monomer followed by the addition of a polymerization catalyst so as to be polymerized by heat or light, and is dispersed in the resin. Or, the surfaces of the thermoplastic resin and the thermosetting resin are dyed with the chromene compound so that it disperses in the resin.

The chromene compound of the present invention can be used as a photochromic material over a wide range, such as various memory materials to substitute for the silver salt photosensitive material, copying material, photosensitive material for printing, memory material for cathode-ray tubes, photosensitive material for laser and photosensitive material for holography. Further, the photochromic material using the chromene compound of the present invention can be used as photochromic lens material, optical filter material, display material, actinometer, ornament, etc. When used as a photochromic lens, for example, there is no particular limitation provided a uniform dimming performance is obtained. Concretely speaking, there can be exemplified a method in which a polymer film in which the photochromic material of the invention is homogeneously dispersed is sandwiched in the lens, a method in which the chromene compound of the invention is dispersed in the polymerizable monomer and is polymerized in a predetermined manner, and a method in which the compound is dissolved in, for example, a silicone oil so that the lens surfaces are impregnated with the compound at 150 to 200° C. for 10 to 60 minutes, and the surfaces are further coated with a curable material to form a photochromic lens. There can be further exemplified a method in which the polymer film is applied onto the lens surfaces which are, then, coated with a curable material to form a photochromic lens.

Photochromic Polymerizable Composition

Among the above photochromic materials, there is used a photochromic polymerizable composition obtained by dispersing the chromene compound of the invention in a polymerizable monomer in producing a photochromic material that comprises a high molecular matrix.

For example, the photochromic polymerizable composition is poured into a predetermined mold and is polymerized by using a polymerization catalyst to obtain a product.

The photochromic polymerizable composition contains a chromene compound of the invention, a polymerizable monomer and, as require, a polymerization initiator.

<Polymerizable Monomer>

As the polymerizable monomer, there can be exemplified those capable of forming a high molecular matrix described above. Among them, a (meth)acrylic acid ester compound is most desired from the standpoint of transparency of the obtained polymer, dimensional stability and workability.

<Polymerization Initiator>

As the polymerization initiator, there is usually used a radical polymerization initiator. Representative examples include diallyl peroxides such as benzoyl peroxide, p-chlorobenzoyl peroxide, decanoyl peroxide, lauroyl peroxide and acetyl peroxide; peroxy esters such as t-butylperoxy-2-ethyl hexanate, t-butylperoxy neodecanate, cumylperoxy neodecanate, t-butylperoxy benzoate, t-butylperoxy isobutylate and 1,1,3,3-tetramethylbutylperoxy-2-ethyl hexanate; percarbonates such as diisopropylperoxy carbonate and di-sec-butylperoxy dicarbonate; and azo compounds such as azobisisobutylonitrile, etc. As the photopolymerization catalyst, there can be exemplified acetophenone compounds such as 1-phenyl-2-hydroxy-2-methylpropane-1-one, 1-hydroxycyclohexylphenylketone, and 1-(4-isopropylphenyl)-2-hydroxy-2-methylpropane-1-one;

α-carbonyl compounds such as 1,2-diphenylethanedione and methylphenyl glyoxylate; and acylphosphinoxide compounds such as 2,6-dimethylbenzoyldiphenyl phosphinoxide, 2,4,6-trimethylbenzoyldiphenyl phosphinoxide, 2,6-dichlorobenzoyldiphenyl phosphinoxide, and 2,6-dimethoxybenzoyl diphenylphosphinoxide. These polymerization initiators may be used alone or in a combination of two or more kinds at any ratio depending upon the monomer that is used. It is further allowable to use a heat polymerization catalyst and a photopolymerization catalyst in combination. When the photopolymerization catalyst is used, a known polymerization promotor such as tertiary amine or the like may be used in combination.

The amount of the polymerization initiator varies depending upon the polymerization conditions, kind of the initiator and composition of the polymerizable monomer, and cannot be definitely stated. Generally, however, the polymerization initiator is used in an amount of from 0.001 to 10 parts by weight and, preferably, from 0.01 to 5 parts by weight per 100 parts by weight of the whole polymerizable monomers.

<Other Components>

The photochromic polymerizable composition of the present invention can be blended with a variety of additives depending upon the use of the photochromic material obtained by polymerizing and curing the polymerizable composition in order to improve its properties but in amounts in which they will not impair the curing of the invention.

For example, the chromene compound used in the present invention can be combined with other known photochromic compound to obtain a photochromic composition. There is no particular limitation on the other photochromic compounds that are to be used in combination, and any known photochromic compound can be used. For example, there can be used, in combination, an oxazine compound, a fulgimide compound and/or a known chromene compound (hereinafter referred to as "other known chromene compound") other than the chromene compound used in the invention.

In the present invention, there is no particular limitation on the mixing ratio of the oxazine compound, fulgimide compound and other known chromene compound, and the mixing ratio may be suitably determined by taking the properties of the photochromic compounds into consideration. When the oxazine compound, fulgimide compound and/or other known chromene compound are to be added to the photochromic polymerizable composition of the present invention, the amount of their addition is usually from 0.001 to 10 parts by weight and, preferably, from 0.01 to 1 part by weight per 100 parts by weight of the whole monomers.

An ultraviolet-ray stabilizer may be added to the photochromic polymerizable composition of the present invention. Addition of the ultraviolet-ray stabilizer further lengthens the durability of photochromic property. In particular, use of the fulgimide compound improves the durability. When a neutral tint is developed by using the oxazine compound and the fulgimide compound in combination, therefore, a change does not occur in the color tone of a neutral tint at the time of developing color even after aged.

As the ultraviolet-ray stabilizer, there can be used any known one without limitation, such as hindered amine photostabilizer, hindered phenol photostabilizer, sulfur-type antioxidant and phosphorous acid ester-type photostabilizer.

Though there is no particular limitation on their amount of use, the ultraviolet-ray stabilizers are usually used in an amount of from 0.01 to 5 parts by weight and, preferably, from 0.02 to 1 part by weight per 100 parts by weight of the whole monomers.

As required, further, there can be added various additives such as benzotriazole-type ultraviolet-ray absorbing agent or benzophenone-type ultraviolet-ray absorbing agent, antioxidant, coloring-preventing agent, antistatic agent, fluorescent dye, pigment and perfume.

<Polymerization and Curing of Polymerizable Composition>

Next, described below is a method of obtaining the photochromic material of the present invention by polymerizing and curing the photochromic polymerizable composition of the present invention.

There is no particular limitation on the polymerization method of obtaining a polymer from the photochromic polymerizable composition of the present invention, and any known polymerization method can be employed. The polymerization means is conducted by using various peroxides and a polymerization initiator such as azo compound, or by the irradiation with ultraviolet rays, α-rays, β-rays or γ-rays, or by utilizing both of them. A representative polymerization method may be a cast polymerization by pouring the photochromic polymerizable composition of the invention containing a radical polymerization initiator into a mold supported by elastomer gaskets or spacers, polymerizing the composition in a heating furnace or by the irradiation with ultraviolet rays or visible light and, then, removing the polymer.

Among the polymerization conditions, the polymerization temperature differs depending upon the kind of the polymerizable monomer and the polymerization initiator and cannot be definitely specified. Usually, however, a so-called tapered two-stage polymerization is conducted by starting the polymerization at a relatively low temperature, slowly raising the temperature and curing the composition at a high temperature at the time when the polymerization has finished. The polymerization time, too, varies depending upon various factors like the temperature and it is desired to determine an optimum time in advance depending upon the conditions. Generally, however, it is desired that the polymerization is completed in 2 to 40 hours.

EXAMPLES

The invention will be described in further detail by way of Examples to which only, however, the invention is in no way limited.

Example 1

1.0 Gram (0.0018 mols) of the following precursor chromene compound,

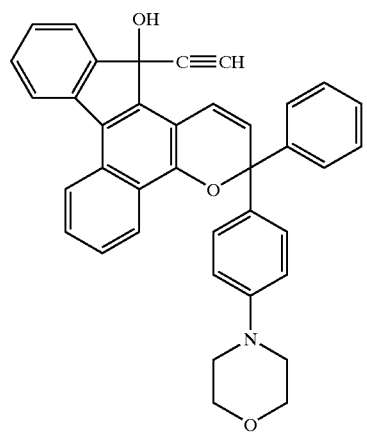

and 0.26 g (0.0018 mols) of the following hydroxynaphthol

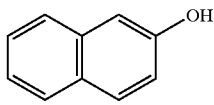

were dissolved in 30 ml of toluene, followed by the addition of 0.05 g of a p-toluenesulfonic acid, and the mixture was stirred at room temperature for one hour. After the reaction, the solvent was removed, and the reaction product was refined by chromatography on silica gel to obtain 0.4 g of a pale yellowish powdery product, yield, 33%.

Elemental analysis of the product showed C 85.60%, H 5.21%, N 2.09%, O 7.10%, which were in very good agreement with the calculated values of C 85.56%, H 5.24%, N 2.08%, O 7.12% of $C_{48}H_{35}NO_3$.

A measurement of a proton nuclear magnetic resonance spectrum indicated a peak of 8H based on a methylene proton of morpholino group near δ3.0 to 4.0 ppm, and a peak of 27H based on an aromatic proton and an alkene proton near δ5.6 to 9.0 ppm.

Further, a measurement of a $^{13}$C-nuclear magnetic resonance spectrum indicated a peak based on a carbon atom of an aromatic ring near δ110 to 160 ppm, a peak based on a carbon atom of an alkene near δ80 to 140 ppm, and a peak based on a carbon atom of an alkyl at δ20 to 60 ppm.

From the above results, it was confirmed that the isolated product was a compound represented by the following structural formula.

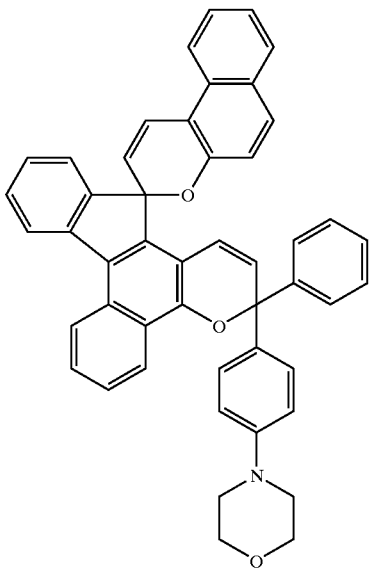

Examples 2 to 13

Chromene compounds shown in Tables 1 to 3 were synthesized in the same manner as in Example 1. The obtained products were analyzed for their structures relying on the same means for confirming structure as that of Example 1. It was confirmed that the obtained products were the compounds represented by the structural formulas shown in Tables 1 to 3. Table 4 shows values of elemental analysis of these compounds, values calculated from the structural formulas of these compounds, and characteristic spectra in $^1$H-NMR spectra.

TABLE 1

| Example No. | Starting material | | Product | Yield (%) |
|---|---|---|---|---|
| | Precursor chromene compound | Hydroxyl derivative product | | |
| 2 | (structure) | (structure) | (structure) | 25 |

TABLE 1-continued
| Example No. | Starting material — Precursor chromene compound | Hydroxyl derivative product | Product | Yield (%) |
|---|---|---|---|---|
| 3 | 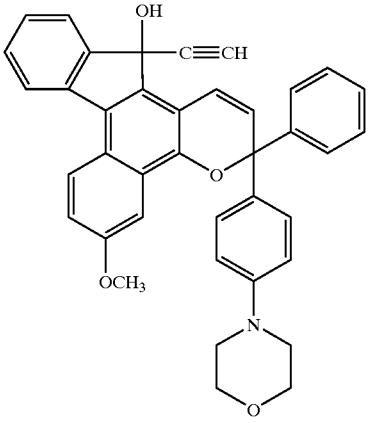 | 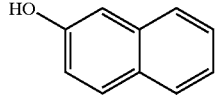 | 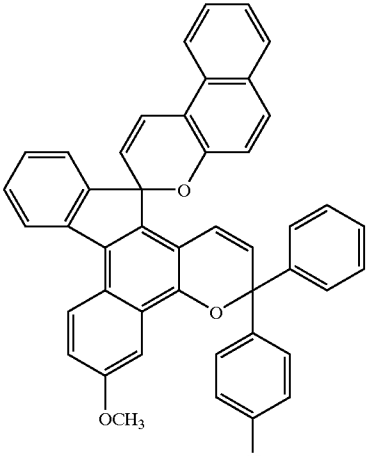 | 23 |
| 4 | 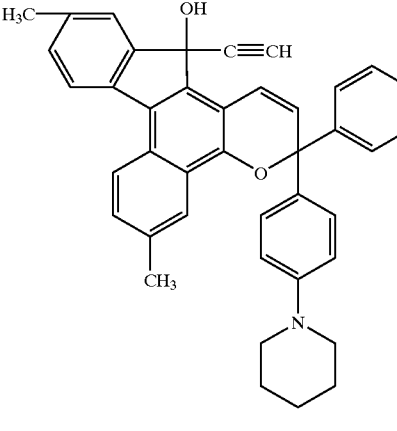 | 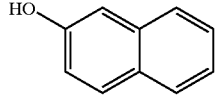 | 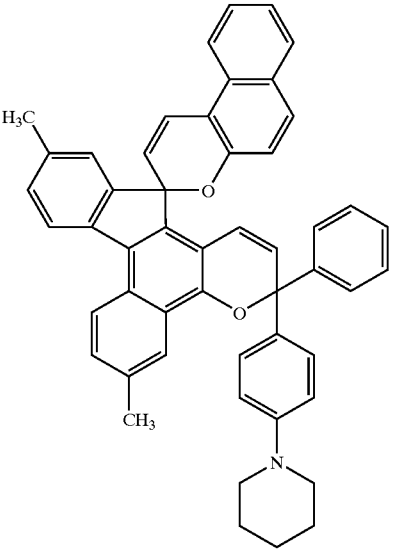 | 22 |
| 5 | 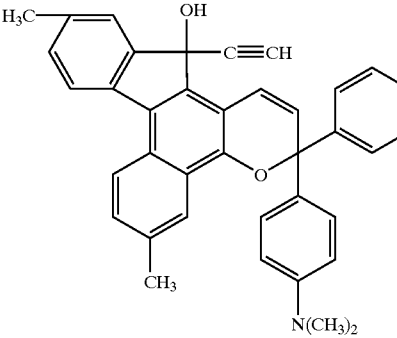 | 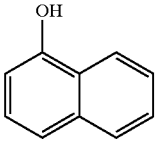 | 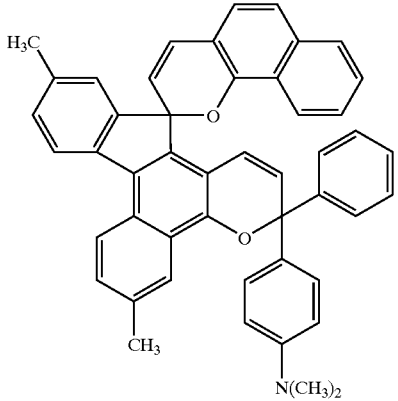 | 21 |

TABLE 2
| Example No. | Starting material — Precursor chromene compound | Hydroxyl derivative product | Product | Yield (%) |
|---|---|---|---|---|
| 6 | 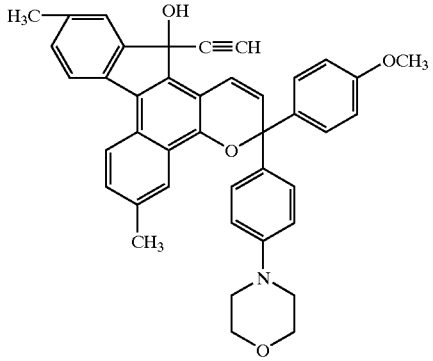 | 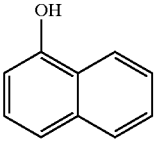 | 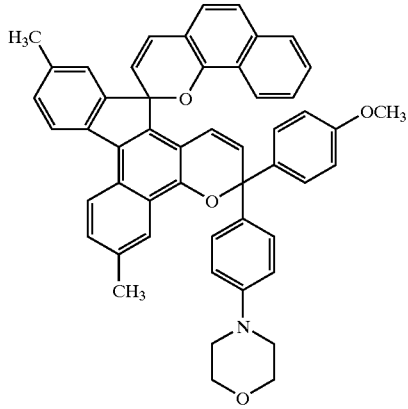 | 24 |
| 7 | 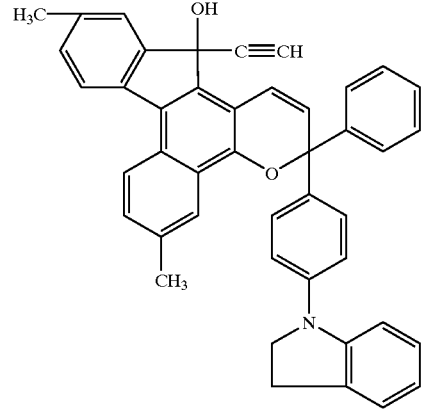 | 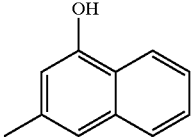 | 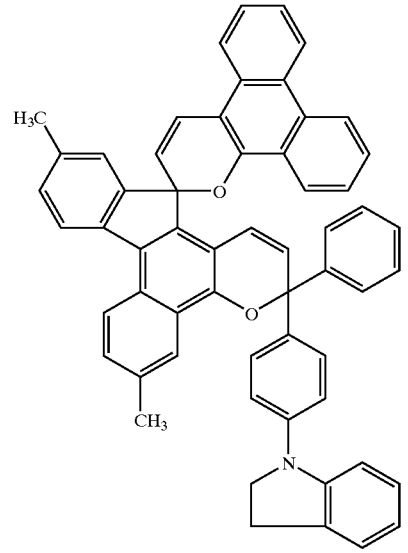 | 19 |
| 8 | 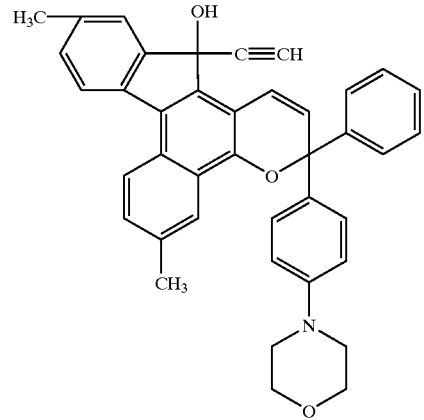 | 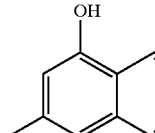 | 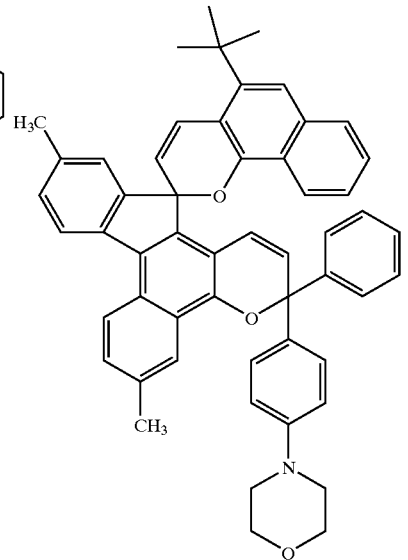 | 12 |

TABLE 2-continued
| Example No. | Starting material | | Product | Yield (%) |
|---|---|---|---|---|
| | Precursor chromene compound | Hydroxyl derivative product | | |
| 9 | 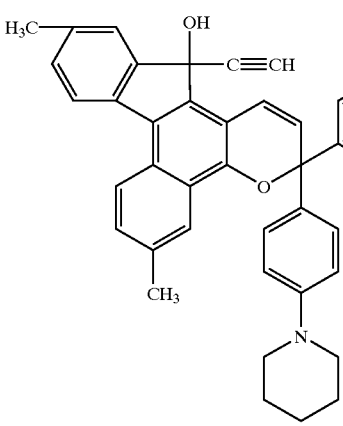 | 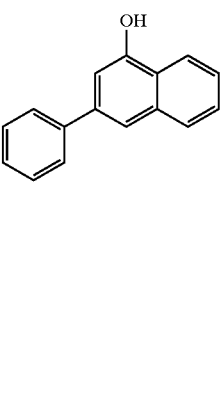 | 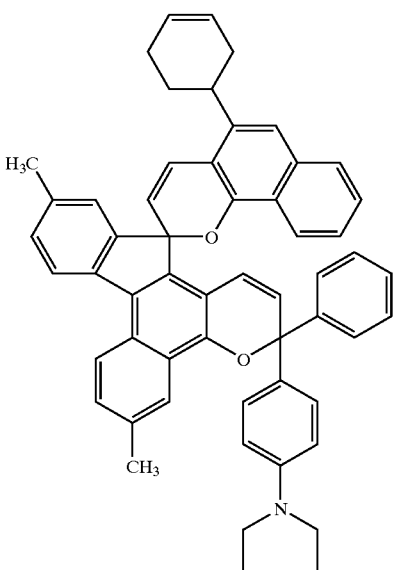 | 10 |
TABLE 3
| Example No. | Starting material | | Product | Yield (%) |
|---|---|---|---|---|
| | Precursor chromene compound | Hydroxyl derivative product | | |
| 10 | 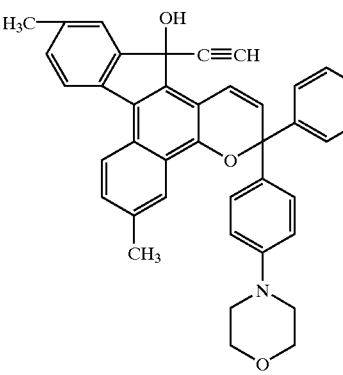 | 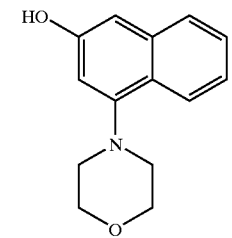 | 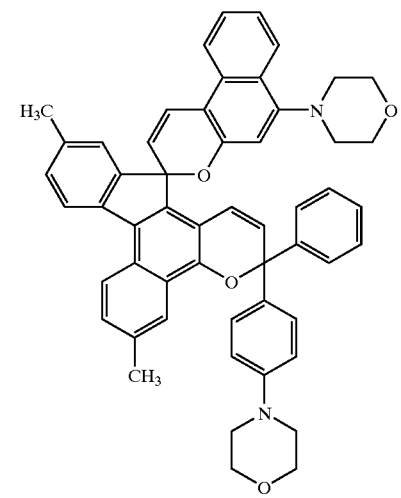 | 30 |

TABLE 3-continued
| Example No. | Starting material | | Product | Yield (%) |
|---|---|---|---|---|
| | Precursor chromene compound | Hydroxyl derivative product | | |
| 11 | 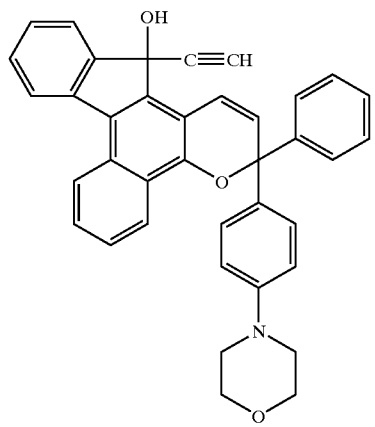 | 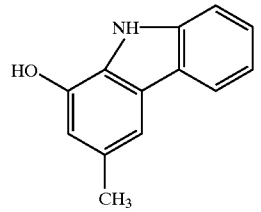 | 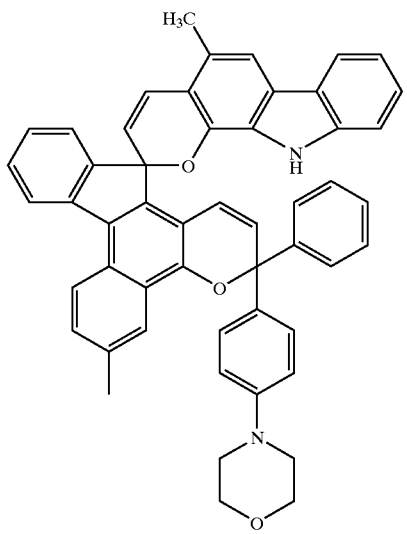 | 20 |
| 12 | 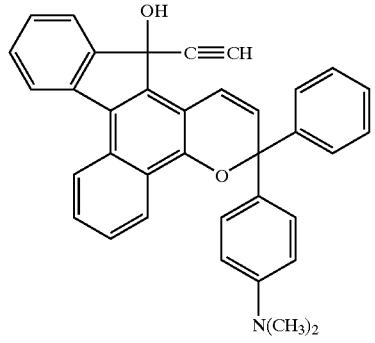 | 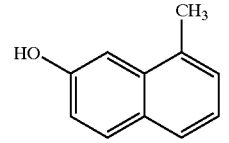 | 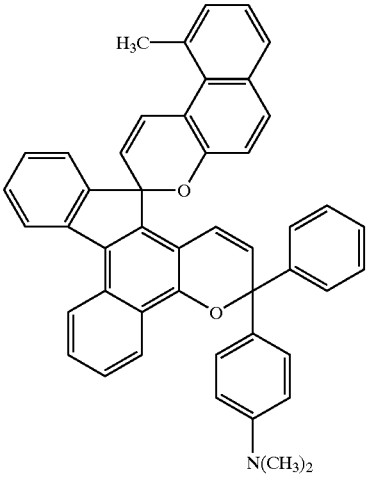 | 25 |
| 13 | 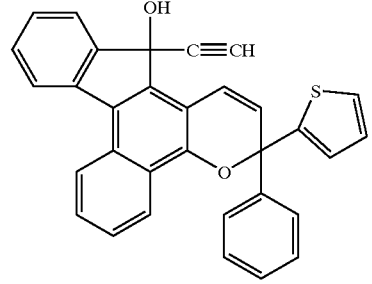 | 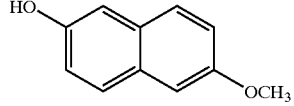 | 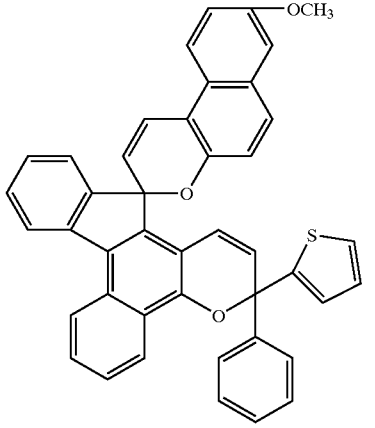 | 22 |

TABLE 4

| Example No. | Found | | | | | Calculated | | | | | 1H-NMR (ppm) |
|---|---|---|---|---|---|---|---|---|---|---|---|
| | C | H | N | O | Others | C | H | N | O | Others | |
| 2 | 85.59 | 5.61 | 1.99 | 6.81 | | 85.56 | 5.60 | 2.00 | 6.84 | | δ 5.6–9.0: 25H |
| | | | | | | | | | | | δ 3.0–4.0: 8H |
| | | | | | | | | | | | δ 1.5–2.5: 6H |
| 3 | 83.64 | 5.32 | 1.97 | 9.07 | | 83.62 | 5.30 | 1.99 | 9.09 | | δ 5.6–9.0: 26H |
| | | | | | | | | | | | δ 3.0–4.0: 11H |
| 4 | 87.55 | 5.92 | 1.98 | 4.54 | | 87.52 | 5.90 | 2.00 | 4.57 | | δ 5.6–9.0: 25H |
| | | | | | | | | | | | δ 3.0–4.0: 4H |
| | | | | | | | | | | | δ 1.5–2.5: 12H |
| 5 | 83.36 | 5.40 | 2.01 | 9.22 | | 83.33 | 5.39 | 2.02 | 9.25 | | δ 5.6–9.0: 25H |
| | | | | | | | | | | | δ 3.0–4.5: 12H |
| 6 | 83.72 | 5.67 | 1.89 | 8.72 | | 83.70 | 5.65 | 1.91 | 8.74 | | δ 5.6–9.0: 24H |
| | | | | | | | | | | | δ 4.0–4.5: 11H |
| | | | | | | | | | | | δ 1.5–2.5: 6H |
| 7 | 88.89 | 5.29 | 1.77 | 4.05 | | 88.86 | 5.27 | 1.79 | 4.08 | | δ 5.6–9.0: 31H |
| | | | | | | | | | | | δ 3.0–4.4: 2H |
| | | | | | | | | | | | δ 1.5–2.8: 8H |
| 8 | 85.61 | 6.27 | 1.83 | 6.31 | | 85.57 | 6.25 | 1.85 | 6.33 | | δ 5.6–9.0: 24H |
| | | | | | | | | | | | δ 3.0–4.5: 8H |
| | | | | | | | | | | | δ 1.2–2.5: 15H |
| 9 | 88.28 | 5.87 | 1.80 | 4.09 | | 88.23 | 5.85 | 1.81 | 4.12 | | δ 5.6–9.0: 29H |
| | | | | | | | | | | | δ 3.0–4.5: 4H |
| | | | | | | | | | | | δ 1.5–2.5: 12H |
| 10 | 82.45 | 5.91 | 3.54 | 8.10 | | 82.42 | 5.89 | 3.56 | 8.13 | | δ 5.6–9.0: 24H |
| | | | | | | | | | | | δ 3.0–4.5: 16H |
| | | | | | | | | | | | δ 1.0–2.5: 6H |
| 11 | 84.31 | 5.29 | 3.83 | 6.58 | | 84.27 | 5.27 | 3.85 | 6.60 | | δ 5.6–11.0: 28H |
| | | | | | | | | | | | δ 2.8–4.5: 8H |
| | | | | | | | | | | | δ 1.0–2.5: 2H |
| 12 | 87.45 | 5.48 | 2.15 | 4.94 | | 87.41 | 5.46 | 2.17 | 4.96 | | δ 5.6–9.0: 27H |
| | | | | | | | | | | | δ 2.8–4.5: 6H |
| | | | | | | | | | | | δ 1.0–2.5: 2H |
| 13 | 82.69 | 4.54 | | 7.66 | S5.11 | 82.67 | 4.52 | | 7.68 | S5.13 | δ 5.6–9.5: 25H |
| | | | | | | | | | | | δ 3.0–4.5: 3H |

Examples 14 to 26

0.05 Parts (parts are by weight) of the chromene compound obtained in Example 1 were added to 70 parts of nonaethylene glycol dimethacrylate, 15 parts of triethylene glycol dimethacrylate, 10 parts of glycidyl methacrylate, 5 parts of 2-hydroxyethyl methacrylate and 1.5 parts of perbutyl ND (manufactured by Nihon Yushi Co.) and were mixed sufficiently. The mixture solution was poured into a mold constituted by glass plates and gaskets of an ethylene/vinyl acetate copolymer, and was cast-polymerized. The polymerization was conducted by using an air furnace, gradually elevating the temperature from 30° C. to 90° C. over 18 hours and maintaining the temperature of 90° C. for 2 hours. After the polymerization, the polymer was removed from the glass mold.

The obtained polymer (2 mm thick) was irradiated with light by using a xenon lamp L-2480 (300W) SHL-100 manufactured by Hamamatsu Photonics Co. through an aeromass filter (manufactured by Coning Co.) at 20±1° C. at beam intensities on the polymer surface of 365 nm =2.4 mW/cm$^2$ and 245 nm=24 μw/cm$^2$ for 120 seconds to develop color and to measure the photochromic properties. The photochromic properties were evaluated in a manner as described below.

① Maximum absorption wavelength (λmax): A maximum absorption wavelength after the development of color as found by using a spectrophotometer (instantaneous multi-channel photodetector MCPD 1000) manufactured by Otsuka Denshi Co. The maximum absorption wavelength is related to the color tone at the time when the color is developed.

② Initial color {ε(0)}: Absorbancy in a state of not being irradiated with light at the maximum absorption wavelength. In an optical material such as spectacle lenses, it can be said that the lower this value, the more excellent the photochromic properties are.

③ Color density {ε(120)−ε(0)}: A difference between an absorbancy {ε(120)} after irradiated with light for 120 seconds at the maximum absorption wavelength and the above ε(0). It can be said that the higher this value, the more excellent the photochromic properties are.

④ Fading rate [t½ (min)]: The time until the absorbancy of a sample at the maximum wavelength drops down to one-half the {ε(120)−ε(0)} from when the sample is no longer irradiated with light after it was irradiated with light for 120 seconds. It can be said that the shorter this time, the more excellent the photochromic properties are.

⑤ Remaining ratio (%)={(A$_{200}$/A$_0$)×100}: The following deterioration promotion testing was conducted in order to evaluate the light resistance of color against the irradiation with light. That is, the obtained polymer (sample) was deteriorated for 200 hours by using a xenon weather meter X25 manufactured by Suga Shikenki Co. The densities of color were evaluated before and after the testing; i.e., the color density ($A_0$) was measured before the testing and the color density ($A_{200}$) was measured after the testing, and a value $\{(A_{200}/A_0) \times 100\}$ was regarded to be a remaining ratio (%) and was used as an index of light resistance of color. The higher the remaining ratio, the higher the light resistance of color.

⑥ Change in the coloring degree ($\Delta YI$)=YI(200)−YI(0): In order to evaluate the light resistance of color tone of when not irradiated with light, the samples before and after the deterioration promotion testing were measured for their color difference by using a color-difference meter (SM-4) manufactured by Suga Shikenki Co. A change in the coloring degree ($\Delta YI$) due to deterioration was found by subtracting a value {YI(0)} of coloring degree of before the testing from a value {YI(200)} of coloring degree of after the testing (after 200 hours) to evaluate the light resistance. The smaller the value $\Delta YI$, the higher the light resistance of color tone of when not irradiated with light.

⑦ Observation of developed color tone: The developed color tone was observed by eyes by causing the obtained polymer to develop color under the sunlight.

The photochromic polymers were obtained in the same manner as described above but using the compounds obtained in Examples 2 to 13 as chromene compounds, and their properties were similarly evaluated. The results were as shown in Table 5.

Comparative Examples 1 to 7

For the purpose of comparison, photochromic polymers were obtained in the same manner as in Example 14 by using the compounds represented by the following formulas (A) to (G). Their properties were as shown in Table 6.

The compound of the formula (A) is a chromene compound disclosed in International Patent Laid-Open WO 96/14596, the compound of the formula (B) is a chromene compound disclosed in International Patent Laid-Open WO 97/48762, and the compounds of the formulas (C) to (E) are chromene compounds disclosed in Examples 4, 7 and 5 of German Patent Application Laid-Open DE 19902771 A1. The compounds of the formulas (F) and (G) are those obtained in the step of study conducted by the present inventors.

(A)

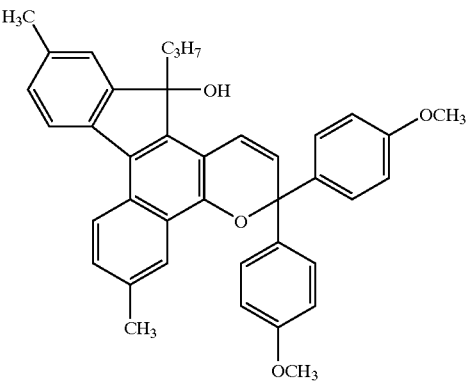

TABLE 5

| Example No. | Compound No. | λmax (nm) | Initial color ε (0) | Color density ε (120) − ε (0) | Fading rate τ ½ (min.) | Light resistance ΔYI | Remaining ratio (%) | Developed color tone |
|---|---|---|---|---|---|---|---|---|
| 14 | 1 | 465 | 0.03 | 0.80 | 2.2 | 2 | 95 | gray |
|  |  | 570 | 0.03 | 1.20 | 2.2 |  | 95 |  |
| 15 | 2 | 470 | 0.03 | 0.90 | 2.0 | 2 | 95 | gray |
|  |  | 578 | 0.03 | 1.30 | 2.0 |  | 95 |  |
| 16 | 3 | 474 | 0.03 | 0.85 | 1.8 | 2 | 94 | gray |
|  |  | 582 | 0.03 | 1.25 | 1.8 |  | 94 |  |
| 17 | 4 | 474 | 0.04 | 1.00 | 1.8 | 2.3 | 94 | gray |
|  |  | 588 | 0.04 | 1.10 | 1.8 |  | 94 |  |
| 18 | 5 | 485 | 0.04 | 0.80 | 1.6 | 2.5 | 93 | gray |
|  |  | 596 | 0.04 | 1.10 | 1.6 |  | 93 |  |
| 19 | 6 | 476 | 0.04 | 0.78 | 1.8 | 2 | 94 | gray |
|  |  | 586 | 0.03 | 1.20 | 1.8 |  | 94 |  |
| 20 | 7 | 470 | 0.04 | 1.15 | 2.5 | 3 | 93 | gray |
|  |  | 588 | 0.03 | 1.45 | 2.5 |  | 93 |  |
| 21 | 8 | 460 | 0.03 | 1.00 | 2.1 | 1.5 | 95 | brown gray |
|  |  | 572 | 0.03 | 0.90 | 2.1 |  | 95 |  |
| 22 | 9 | 476 | 0.03 | 0.88 | 1.9 | 2.4 | 93 | gray |
|  |  | 586 | 0.03 | 1.05 | 1.9 |  | 93 |  |
| 23 | 10 | 450 | 0.05 | 1.20 | 2.0 | 3.5 | 92 | brown |
|  |  | 574 | 0.04 | 1.00 | 2.0 |  | 92 |  |
| 24 | 11 | 465 | 0.04 | 1.30 | 3.2 | 3 | 92 | brown gray |
|  |  | 590 | 0.04 | 1.40 | 3.2 |  | 92 |  |
| 25 | 12 | 452 | 0.03 | 0.76 | 1.5 | 3.5 | 92 | gray |
|  |  | 600 | 0.03 | 0.95 | 1.5 |  | 92 |  |
| 26 | 13 | 440 | 0.04 | 0.80 | 3.5 | 2 | 92 | gray |
|  |  | 565 | 0.04 | 1.05 | 3.5 | 2 | 92 |  |

37
-continued
(B)
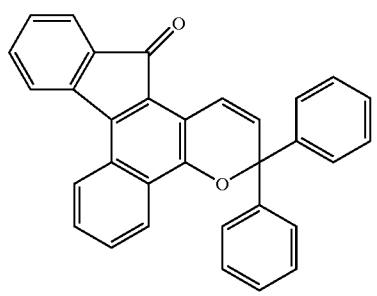
(C)
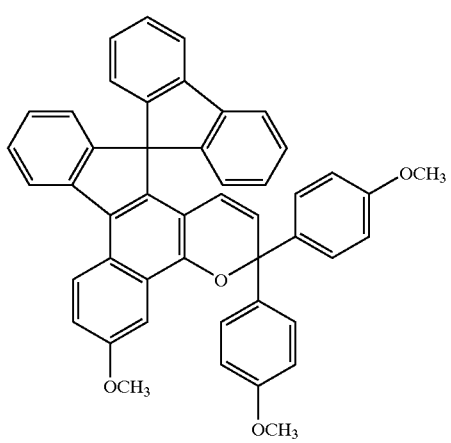
(D)
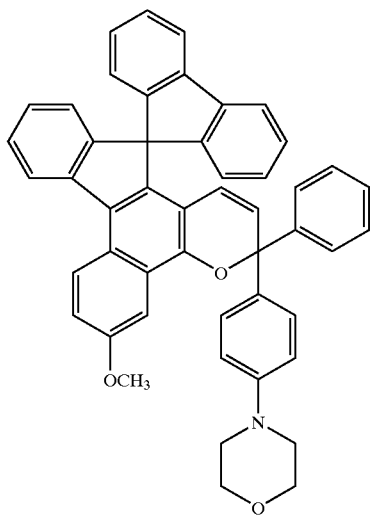
38
-continued
(E)
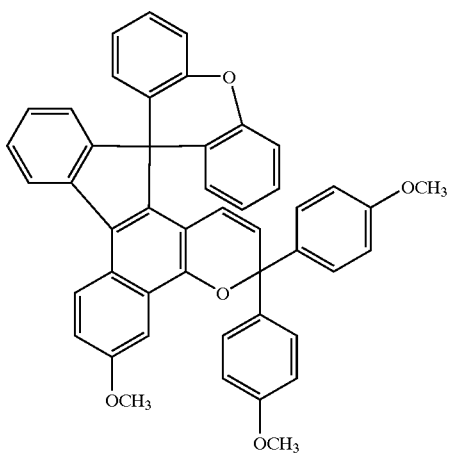
(F)
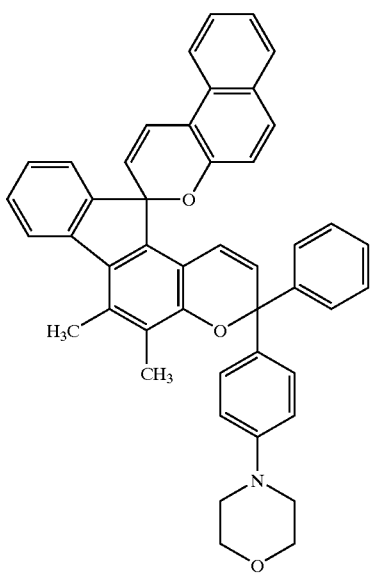
(G)
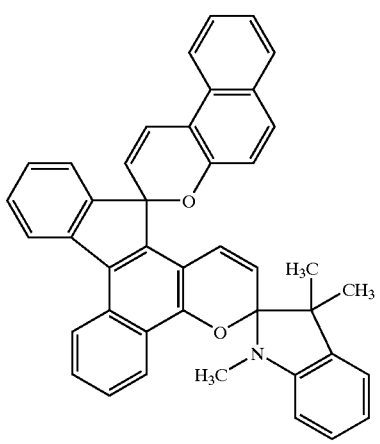

TABLE 6

| Comparative Example No. | Compound No. | λmax (nm) | Initial color ε (0) | Color density ε (120) − ε (0) | Fading rate τ ½ (min.) | Light resistance ΔYI | Light resistance Remaining ratio (%) | Developed color tone |
|---|---|---|---|---|---|---|---|---|
| 1 | (A) | 440 | 0.03 | 0.40 | 10.0 | 8 | 73 | violet |
|   |     | 570 | 0.03 | 0.50 | 10.0 |   | 73 |   |
| 2 | (B) | 425 | 0.05 | 0.20 | 15.0 | 15 | 70 | reddish-violet |
|   |     | 536 | 0.03 | 0.30 | 15.0 |    | 70 |   |
| 3 | (C) | 460 | 0.03 | 0.70 | 5.0 | 3 | 90 | blue |
|   |     | 575 | 0.03 | 1.00 | 5.0 |   | 90 |   |
| 4 | (D) | 470 | 0.03 | 0.70 | 4.5 | 3 | 85 | blue |
|   |     | 580 | 0.03 | 1.00 | 4.5 | 3 | 85 |   |
| 5 | (E) | 460 | 0.03 | 0.60 | 5.0 | 4 | 80 | blue |
|   |     | 576 | 0.03 | 1.00 | 5.0 | 4 | 80 |   |
| 6 | (F) | 440 | 0.05 | 0.20 | 0.9 | 15 | 40 | red |
|   |     | 514 | 0.03 | 0.30 | 0.9 |    | 40 |   |
| 7 | (G) | 440 | 0.05 | 0.20 | 1.2 | 20 | 10 | green |
|   |     | 610 | 0.1  | 0.50 | 1.2 |    | 10 |   |

In Examples 14 to 26 using the chromene compounds of the present invention, the photochromic polymers exhibit larger fading rates, less color after aged and more excellent photochromic light resistance than those of Comparative Examples 1 and 2.

As demonstrated by Comparative Examples 3 to 7, further, even the chromene compounds having structures similar to that of the chromene compound of the present invention exhibit fading rates inferior to that of the chromene compound of the present invention when the ring that is spiro-bonded to the indene ring is not a condensed ring having a pyran skeleton (Comparative Examples 3, 4 and 5).

Even when the ring that is spiro-bonded to the indene ring is the condensed ring having a pyran skeleton like that of the present invention, the fading rate is inferior to that of the chromene compound of the present invention when a divalent group is not bonded to the carbon atoms at the fifth and sixth positions of the chromene ring to form a ring (Comparative Example 6) and when a substituent bonded to the carbon atom at the second position of the chromene ring is the one other than those represented by R5 and R6 of the above general formula (1)(Comparative Example 7).

The chromene compound of the present invention develops a color tone of a neutral tint by itself, exhibits a small initial color, offers a high color density, exhibits excellent light resistance and, further, exhibits a large fading rate even when it is dispersed in a solution or in a high molecular solid matrix, which are excellent photochromic properties.

When a photochromic lens is prepared by using the chromene compound of the present invention, therefore, a color tone of a neutral tint can be obtained without using many other photochromic compounds in combination. Thus, there is obtained a photochromic lens of which the color fades quickly when it is brought indoors from outdoors and which offers a large light resistance enabling the lens to be used for extended periods of time.

What is claimed is:

1. A chromene compound represented by the following general formula (1),

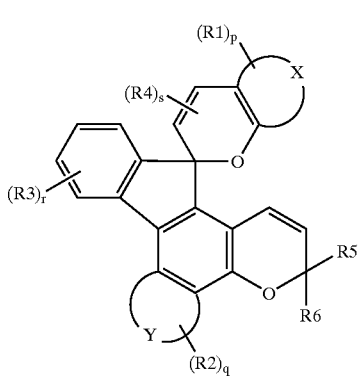

wherein a divalent group represented by the following formula (2),

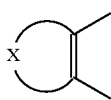

and a divalent group represented by the following formula (3),

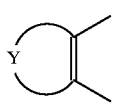

are aromatic hydrocarbon groups or unsaturated heterocyclic groups independently from each other;
 a substituent R1 of the group represented by the above formula (2) is an alkyl group, a hydroxyl group, an alkoxyl group, an aralkoxyl group, an amino group, a substituted amino group, a cyano group, a nitro group, substituted or unsubstituted aryl group, a halogen atom, a trifluoromethyl group, an aralkyl group, a monovalent heterocyclic group bonded to the ring of the group represented by the above formula (2) through the carbon atom, a monovalent substituted or unsubstituted heterocyclic group having a nitrogen atom as a hetero atom and bonded to the ring of the group represented by the above formula (2) through said nitrogen atom, or a monovalent condensed heterocyclic group in which said heterocyclic group is condensed with an aromatic hydrocarbon ring or an aromatic heterocyclic ring, and p is an integer of 0 to 3;

a substituent R2 of the group represented by the above formula (3) is an alkyl group, a hydroxyl group, an alkoxyl group, an aralkoxyl group, an amino group, a substituted amino group, a cyano group, a nitro group, substituted or unsubstituted aryl group, a halogen atom, a trifluoromethyl group, an aralkyl group, a monovalent heterocyclic group bonded to an indene ring through the carbon atom, a monovalent substituted or unsubstituted heterocyclic group having a nitrogen atom as a hetero atom and bonded to the ring of the group represented by the above formula (3)through said nitrogen atom, or a monovalent condensed heterocyclic group in which said heterocyclic group is condensed with an aromatic hydrocarbon ring or an aromatic heterocyclic ring, and q is an integer of 0 to 3;

a substituent R3 of the indene ring is an alkyl group, a hydroxyl group, an alkoxyl group, an aralkoxyl group, an amino group, a substituted amino group, a cyano group, a nitro group, substituted or unsubstituted aryl group, a halogen atom, a trifluoromethyl group, an aralkyl group, a monovalent heterocyclic group bonded to the indene ring through the carbon atom, a monovalent substituted or unsubstituted heterocyclic group having a nitrogen atom as a hetero atom and bonded to the indene ring through said nitrogen atom, or a monovalent condensed heterocyclic group in which said heterocyclic group is condensed with an aromatic hydrocarbon ring or an aromatic heterocyclic ring, and r is an integer of 0 to 3;

a substituent R4 of the pyran ring is an alkyl group, a hydroxyl group, an alkoxyl group, an aralkoxyl group, an amino group, a substituted amino group, a cyano group, a nitro group, a substituted or unsubstituted aryl group, a halogen atom, a trifluoromethyl group, an aralkyl group a monovalent heterocyclic group bonded to the pyran ring through the carbon atom, is a monovalent substituted or unsubstituted heterocyclic group having a nitrogen atom as a hetero atom and bonded to the pyran ring through said nitrogen atom, or a monovalent condensed heterocyclic group in which said heterocyclic group is condensed with an aromatic hydrocarbon ring or an aromatic heterocyclic ring, and s is an integer of 0 to 3;

each of R5 and R6 is, independently from each other, groups represented by the following formula (4),

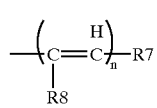

(4)

wherein R7 is a substituted or unsubstituted aryl group or a substituted or unsubstituted heteroaryl group, R8 is a hydrogen atom, an alkyl group or a halogen atom, and n is an integer of 1 to 3;

a group represented by the following formula (5),

(5)

wherein R9 is a substituted or unsubstituted aryl group or a substituted or unsubstituted heteroaryl group, and m is an integer of 1 to 3;

a substituted or unsubstituted aryl group, substituted or unsubstituted heteroaryl group, or an alkyl group, wherein R5 and R6 together may constitute an aliphatic hydrocarbon ring or an aromatic hydrocarbon ring.

2. A chromene compound represented by the following general formula (6),

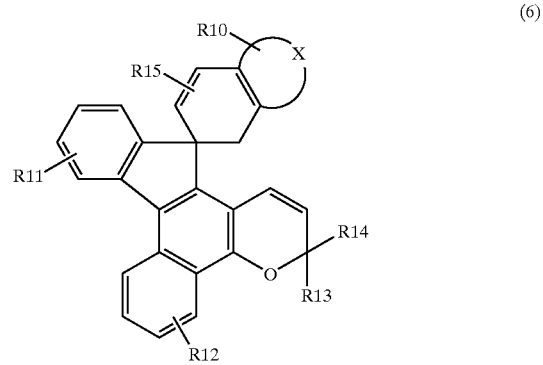

(6)

wherein a divalent group represented by the following formula (2),

(2)

is an aromatic hydrocarbon group or an unsaturated heterocyclic group;

each of R10, R11, R12 and R15 is, independently from each other, a hydrogen atom; an alkyl group having 1 to 4 carbon atoms; an alkoxyl group having 1 to 5 carbon atoms; an aralkoxyl group having 6 to 10 carbon atoms; a mono-substituted or di-substituted amino group having, as a substituent, an alkyl group with 1 to 4 carbon atoms or an aryl group with 6 to 10 carbon atoms; a cyano group; an aryl group having 6 to 10 carbon atoms; a substituted aryl group having 6 to 10 carbon atoms (without including carbon atoms of the substituent) and having, as a substituent, an alkyl group having 1 to 4 carbon atoms or an alkoxy group having 1 to 5 carbon atoms; a halogen atom; a substituted or unsubstituted heterocyclic group having a nitrogen atom as a hetero atom and bonded to a ring of the group represented by the above formula (2) or to the indene ring, pyran ring or naphthalene ring through the nitrogen atom; or a condensed heterocyclic group in which said heterocyclic group is condensed with an aromatic hydrocarbon ring or an aromatic heterocyclic ring; and each of R13 and R14 is, independently from each other, an aryl groups having 6 to 10 carbon atoms; or a substituted aryl group having, as a substituent, (i) an alkyl group with 1 to 4 carbon atoms (ii) an alkoxy group with 1 to 5 carbon atoms, (iii) a substituted or unsubstituted heterocyclic group which has a nitrogen atom as a hetero atom and is bonded to the aryl group through the nitrogen atom, or (iv) a condensed hetrocyclic group in which said heterocyclic group is condensed with an aromatic hydrocarbon ring or an aromatic heterocyclic ring; said substituted aryl group having 6 to 10 carbon atoms (without including the carbon atoms of the substituent).

3. A chromene compound according to claim 2, wherein:

the group represented by the above formula (2) is an aromatic hydrocarbon group having 6 to 18 carbon atoms; and one of R13 and R14 is a substituted aryl group having at least one substituent selected from the group consisting of (a) a mono-substituted or di-substituted amino group which has, as a substituent, an alkyl group with 1 to 4 carbon atoms or an aryl group with 6 to 10 carbon atoms, (b) a morpholino group, (c) a piperidino group, (d) a pyrrolidinyl group, (e) a piperadino group, (f) an N-methylpiperadino group and (g) an indolinyl group, said substituted aryl group having 6 to 10 carbon atoms (without including carbon atoms of the substituent), and the other one is an aryl group with 6 to 10 carbon atoms.

4. A photochromic material containing the chromene compound of claim 1.

5. A photochromic optical material containing the chromene compound of claim 1.

6. A photochromic polymerizable composition containing a chromene compound of claim 1 and a polymerizable monomer.

7. A photochromic polymerizable composition according to claim 6, further containing a polymerization initiator.

8. A photochromic polymerizable composition according to claim 6, wherein the polymerizable monomer is a (meth)acrylic acid ester compound.

9. A photochromic material containing the chromene compound of claim 2.

10. A photochromic optical material containing the chromene compound of claim 2.

11. A photochromic polymerizable composition containing a chromene compound of claim 2 and a polymerizable monomer.

12. A photochromic polymerizable composition according to claim 11, further containing a polymerization initiator.

13. A photochromic polymerizable composition according to claim 11, wherein the polymerizable monomer is a (meth)acrylic acid ester compound.

14. A photochromic polymerizable composition according to claim 12, wherein the polymerizable monomer is a (meth)acrylic acid ester compound.

* * * * *